US012383204B2

(12) United States Patent
Garrett et al.

(10) Patent No.: US 12,383,204 B2
(45) Date of Patent: Aug. 12, 2025

(54) METHOD AND SYSTEM FOR AUTOMATED QUANTIFICATION OF SIGNAL QUALITY

(71) Applicant: Analytics For Life Inc., Toronto (CA)

(72) Inventors: Michael Garrett, Wilmette, IL (US); Timothy William Fawcett Burton, Toronto (CA); Shyamlal Ramchandani, Kingston (CA); Abhinav Doomra, Toronto (CA)

(73) Assignee: Analytics For Life Inc., Toronto (CA)

( * ) Notice: Subject to any disclaimer, the term of this patent is extended or adjusted under 35 U.S.C. 154(b) by 513 days.

(21) Appl. No.: 16/725,416

(22) Filed: Dec. 23, 2019

(65) Prior Publication Data

US 2020/0205739 A1 Jul. 2, 2020

Related U.S. Application Data

(60) Provisional application No. 62/784,962, filed on Dec. 26, 2018.

(51) Int. Cl.
*A61B 5/00* (2006.01)
*A61B 5/024* (2006.01)
*A61B 5/318* (2021.01)
*A61B 5/369* (2021.01)
*G06F 17/14* (2006.01)
*G16H 40/67* (2018.01)
*G16H 50/20* (2018.01)
*G16H 50/30* (2018.01)

(52) U.S. Cl.
CPC .......... *A61B 5/7221* (2013.01); *A61B 5/7203* (2013.01); *G16H 40/67* (2018.01); *G16H 50/20* (2018.01); *G16H 50/30* (2018.01); *A61B 5/02416* (2013.01); *A61B 5/318* (2021.01); *A61B 5/369* (2021.01); *G06F 17/142* (2013.01)

(58) Field of Classification Search
USPC .......................................................... 702/19
See application file for complete search history.

(56) References Cited

U.S. PATENT DOCUMENTS

| | | | |
|---|---|---|---|
| 8,923,958 B2 | 12/2014 | Gupta et al. | |
| 9,289,150 B1 | 3/2016 | Gupta et al. | |
| 9,408,543 B1 | 8/2016 | Gupta et al. | |
| 9,597,021 B1 | 3/2017 | Gupta et al. | |
| 9,655,536 B2 | 5/2017 | Gupta et al. | |
| 9,681,844 B2* | 6/2017 | Xu | A61B 5/25 |
| 9,737,229 B1 | 8/2017 | Gupta et al. | |
| 9,910,964 B2 | 3/2018 | Burton et al. | |
| 9,955,883 B2 | 5/2018 | Gupta et al. | |
| 9,968,265 B2 | 5/2018 | Burton et al. | |
| 9,968,275 B2 | 5/2018 | Gupta et al. | |
| 10,039,468 B2 | 8/2018 | Gupta et al. | |
| 10,292,596 B2 | 5/2019 | Shadforth et al. | |
| 2007/0260151 A1 | 11/2007 | Clifford | |
| 2009/0143693 A1 | 6/2009 | Ye et al. | |
| 2010/0249662 A1 | 9/2010 | Shimizu | |
| 2013/0096304 A1 | 4/2013 | Gupta et al. | |
| 2013/0211224 A1 | 8/2013 | Isenhart et al. | |
| 2014/0207017 A1 | 7/2014 | Gilmore et al. | |
| 2016/0015286 A1 | 1/2016 | Gitlin et al. | |
| 2016/0242664 A1 | 8/2016 | Wang et al. | |
| 2017/0055920 A1* | 3/2017 | Mestha | G06T 7/246 |
| 2017/0119272 A1 | 5/2017 | Gupta et al. | |
| 2018/0000371 A1 | 1/2018 | Gupta et al. | |
| 2018/0078146 A1 | 3/2018 | Shadforth et al. | |
| 2018/0249960 A1 | 9/2018 | Gupta et al. | |
| 2018/0325457 A1 | 11/2018 | Ghosh et al. | |
| 2018/0350468 A1 | 12/2018 | Friedman et al. | |
| 2019/0117164 A1 | 4/2019 | Gupta et al. | |
| 2019/0200893 A1 | 7/2019 | Grouchy et al. | |
| 2019/0214137 A1 | 7/2019 | Gupta et al. | |
| 2019/0365265 A1 | 12/2019 | Grouchy et al. | |
| 2019/0384757 A1 | 12/2019 | Garrett et al. | |

FOREIGN PATENT DOCUMENTS

| | | |
|---|---|---|
| CN | 101449973 A | 6/2009 |
| CN | 105210107 A | 12/2015 |
| CN | 105611872 A | 5/2016 |
| CN | 105997064 A | 10/2016 |
| CN | 107550484 A | 1/2018 |
| JP | 2010-220947 A | 10/2010 |
| JP | 2016-536044 A | 11/2016 |
| JP | 2017-143911 A | 8/2017 |
| JP | 2018-528812 A | 2/2018 |

(Continued)

OTHER PUBLICATIONS

Singh, B. et al; "Various approaches to minimise noises in ECG signal: A survey." 2015 Fifth International Conference on Advanced Computing & Communication Technologies. IEEE, 2015; p. 131-137 (Year: 2015).*

Nikolaev, N., et al. "Suppression of electromyogram interference on the electrocardiogram by transform domain denoising." Medical and Biological Engineering and Computing 39.6 (2001): 649-655 (Year: 2001).*

Gaiseanu, Florin. "Evaluating attitude and behavior: An info-operational procedure related/supported by the cognitive centers of mind." International Journal on Neuropsychology and Behavioural Sciences 2.1 (2021): 1-5 (Year: 2021).*

(Continued)

*Primary Examiner* — G. Steven Vanni

(74) *Attorney, Agent, or Firm* — Meunier Carlin & Curfman LLC

(57) ABSTRACT

Systems and methods for the quantification of the quality of an acquired signal are provided for assessment and for gating the acquired signal for subsequent analysis. A signal is acquired, and a determination is made in real-time if there is a problem with the acquisition. If there is a problem, output is provided via the systems and methods described herein to indicate that signal acquisition needs to be performed again.

17 Claims, 24 Drawing Sheets

(56) References Cited

FOREIGN PATENT DOCUMENTS

| JP | 2018-82893 A | 5/2018 | |
|---|---|---|---|
| JP | 2018-526088 A | 9/2018 | |
| WO | 2014200856 A1 | 12/2014 | |
| WO | WO 2015/048514 A1 * | 2/2015 | ........... A61B 5/0245 |
| WO | 2015052609 | 4/2015 | |
| WO | 2015117035 A1 | 8/2015 | |
| WO | 2017/033164 | 3/2017 | |
| WO | 2017033140 A1 | 3/2017 | |
| WO | 2017033164 A1 | 3/2017 | |
| WO | 2017/221221 | 12/2017 | |

OTHER PUBLICATIONS

Abacherli, R et al; "Suppression of MR gradient artefacts on electrophysiological signals based on an adaptive real-time filter with LMS coefficient updates", MAGMA (2005) 18: 41-50 (Year: 2005).*

Santosh I. Patel, Michael J. Souter, David S. Warner, Mark A. Warner; "Equipment-related Electrocardiogramafacts: Causes, Characteristics, Consequences, and Correction." Anesthesiology 2008; 108:138-148 (Year: 2008).*

Abächerli, Roger, et al. "Suppression of MR gradient artefacts on electrophysiological signals based on an adaptive real-time filter with LMS coefficient updates." Magnetic Resonance Materials in Physics, Biology and Medicine 18 (2005): 41-50. (Year: 2005).*

Liang, Yongbo, et al. "Hypertension assessment via ECG and PPG signals: An evaluation using MIMIC database." Diagnostics 8.3 (2018): 65. (Year: 2018).*

Oster, Julien, and Gari D. Clifford. "Acquisition of electrocardiogram signals during magnetic resonance imaging." Physiological measurement 38.7 (2017): R119. (Year: 2017).*

Patel, Santosh I., et al. "Equipment-related electrocardiogramtifacts: causes, characteristics, consequences, and correction." The Journal of the American Society of Anesthesiologists 108.1 (2008): 138-148. (Year: 2008).*

Thamarai, P., and K. Adalarasu. "Denoising of EEG, ECG and PPG signals using wavelet transform." Journal of Pharmaceutical Sciences and Research 10.1 (2018): 156-161. (Year: 2018).*

Extended Search Report, dated Aug. 5, 2022, received in connection with corresponding EP Patent Application No. 19903193.1.

Cooley, J., et al., "An Algorithm for the Machine Calculation of Complex Fourier Series," Mathematics of Computation, vol. 19, No. 90, 1965, pp. 297-301.

MATLAB MathWorks: z-score, retrieved on Apr. 20, 2020, at https://www.mathworks.com/help/stats/zscore.html, 2018, 11 pages.

Qayyum, H., et al., "Facial Expression Recognition Using Stationary Wavelet Transform Features," Hindawi, Mathematical Problems in Engineering, 2017, 9 pages.

Rimm, E.B., et al., "Body Size and Fat Distribution as Predictors of Coronary Heart Disease among Middle-aged and Older US Men," American Journal of Epidemiology, vol. 141, Issue 12, 1995, pp. 1117-1127.

International Search Report and Written Opinion, dated Feb. 28, 2020, received in connection with corresponding International Patent Application No. PCT/IB2019/061313.

Office Action issued in Japanese Patent Application No. 2021-537824, issued Nov. 8, 2023, 13 pages.

Office Action issued in Japanese Patent Application No. 2021-537824, issued Apr. 23, 2024, 8 pages.

First Office Action issued in Chinese Patent Application No. 2019800930548, issued Dec. 27, 2023, 16 pages.

Office Action issued in Chinese Patent Application No. 2019800930548, issued Jul. 3, 2024, 17 pages.

Urigüen, Jose Antonio, and Begoña Garcia-Zapirain. "EEG artifact removal—state-of-the-art and guidelines." Journal of neural engineering 12.3 (2015): 031001.

Communication Pursuant to Article 94(3) EPC issued for European Application No. 19903193.1, dated Feb. 6, 2025.

Office Action issued issued for Canadian Application No. 3124751, dated Jan. 23, 2025.

* cited by examiner

METHOD AND SYSTEM FOR AUTOMATED QUANTIFICATION OF SIGNAL QUALITY

RELATED APPLICATION

This U.S. patent application claims priority to, and the benefit of, U.S. Patent Provisional Application No. 62/784,962, filed Dec. 26, 2018, entitled "Method and System for Automated Quantification of Signal Quality," which is incorporated by reference herein in its entirety.

FIELD OF THE INVENTION

The present disclosure generally relates to non-invasive methods and systems for characterizing cardiovascular circulation and other physiological systems. More specifically, in an aspect, the present disclosure relates to the quality assessment of an acquired biophysical signal (e.g., a cardiac signal, a brain/neurological signal, signals associated with other biological systems, etc.) and the gating of the acquired signal for analysis.

BACKGROUND

Ischemic heart disease, also known as cardiac ischemia or myocardial ischemia, is a disease or group of diseases characterized by a reduced blood supply to the heart muscle, usually due to coronary artery disease (CAD). CAD typically occurs when the lining inside the coronary arteries that supply blood to the myocardium, or heart muscle, develops atherosclerosis (the hardening or stiffening of the lining and the accumulation of plaque therein, often accompanied by abnormal inflammation). Over time, CAD can also weaken the heart muscle and contribute to, e.g., angina, myocardial infarction (cardiac arrest), heart failure, and arrhythmia. An arrhythmia is an abnormal heart rhythm and can include any change from the normal sequence of electrical conduction of the heart and in some cases can lead to cardiac arrest.

The evaluation of CAD can be complex, and many techniques and tools are used to assess the presence and severity of the condition. In the case of electrocardiography, a field of cardiology in which the heart's electrical activity is analyzed to obtain information about its structure and function, significant ischemic heart disease can alter ventricular conduction properties of the myocardium in the perfusion bed downstream of a coronary artery narrowing or occlusion. This pathology can express itself at different locations of the heart and at different stages of severity, making an accurate diagnosis challenging. Further, the electrical conduction characteristics of the myocardium may vary from person to person, and other factors such as measurement variability associated with the placement of measurement probes and parasitic losses associated with such probes and their related components can also affect the biophysical signals that are captured during electrophysiologic tests of the heart. Further still, when conduction properties of the myocardium are captured as relatively long cardiac phase gradient signals, they may exhibit complex nonlinear variability that cannot be efficiently captured by traditional modeling techniques.

Signal quality of acquired biophysical signals, whether cardiac signals, neurological signals, or other biophysical signals, can be affected by noise. Such noise, which can originate from a variety of sources, can affect the assessment of the patient, including the clinical assessment of the patient's biological system or systems associated with such signals and any associated conditions or pathologies. In the case of cardiac signals, such noise may affect some or all of the acquired signals, reducing the efficacy of the assessment for CAD, arrythmia, pulmonary hypertension, heart failure—e.g., any condition or symptom associated with, related to, or affected by (directly or indirectly) cardiac signals and thus putting the patient at risk of an incorrect assessment and/or diagnosis.

In addition, if a problem such as poor signal quality adversely does affect, some or all of the acquired signals may have to be disregarded and new signals acquired from the patient. In some instances, this may result the assessment having to be re-acquired, causing inconvenience to the patient inconveniently in having to come back to the physician's office, hospital, or other clinical setting, and additional cost to the healthcare system.

SUMMARY

The exemplified methods and systems described herein facilitate the quantification of signal quality of an acquired signal for assessment and for gating the acquired signal for subsequent analysis.

As used herein, the term "cardiac signal" refers to one or more signals associated with the structure, function and/or activity of the cardiovascular system—including aspects of that signal's electrical/electrochemical conduction—that, e.g., cause contraction of the myocardium. A cardiac signal may include, in some embodiments, electrocardiographic signals such as, e.g., those acquired via an electrocardiogram (ECG) or other modalities.

As used herein, the term "neurological signal" refers to one or more signals associated with the structure, function and/or activity of the central and peripheral nervous systems, including the brain, spinal cord, nerves, and their associated neurons and other structures, etc., and including aspects of that signal's electrical/electrochemical conduction. A neurological signal may include, in some embodiments, electroencephalographic signals such as, e.g., those acquired via an electroencephalogram (EEG) or other modalities.

As used herein, the term "biophysical signal" is not limited to a cardiac signal, a neurological signal or a photoplethysmographic signal but encompasses any physiological signal from which information may be obtained. Not intending to be limited by example, one may classify biophysical signals into types or categories that can include, for example, electrical (e.g., certain cardiac and neurological system-related signals that can be observed, identified and/or quantified by techniques such as the measurement of voltage/potential, impedance, resistivity, conductivity, current, etc. in various domains such as time and/or frequency), magnetic, electromagnetic, optical (e.g. signals that can be observed, identified and/or quantified by techniques such as reflectance, interferometry, spectroscopy, absorbance, transmissivity, visual observation, photoplethysmography, and the like), acoustic, chemical, mechanical (e.g., signals related to fluid flow, pressure, motion, vibration, displacement, strain), thermal, and electrochemical (e.g. signals that can be correlated to the presence of certain analytes, such as glucose). Biophysical signals may in some cases be described in the context of a physiological system (e.g., respiratory, circulatory (cardiovascular, pulmonary), nervous, lymphatic, endocrine, digestive, excretory, muscular, skeletal, renal/urinary/excretory, immune, integumentary/exocrine and reproductive systems), an organ system (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radicals, inorganic ions, minerals, acids, and other compounds, elements and their subatomic components. Unless stated otherwise, the term "biophysical signal acquisition" generally refers to any passive or active means of acquiring a biophysical signal from a physiological system, such as a mammalian or non-mammalian organism. Passive biophysical signal acquisition generally refers to the observation of natural or induced electrical, magnetic, optical, and/or acoustics emittance of the body tissue. Non-limiting examples of passive and active biophysical signal acquisition means includes, e.g., voltage/potential, current, magnetic, acoustic, optical and other non-active ways of observing the natural emittance of the body tissue, and in some instances, inducing such emittance. Non-limiting examples of passive and active biophysical signal acquisition means include. e.g., ultrasound, radio waves, microwaves, infrared and/or visible light (e.g., for use in pulse oximetry or photoplethysmography), visible light, ultraviolet light and other ways of actively interrogating the body tissue that does not involve ionizing energy or radiation (e.g., X-ray). Active biophysical signal acquisition may also involve transmitting ionizing energy or radiation (e.g., X-ray) (also referred to as "ionizing biophysical signal") to the body tissue. Passive and active biophysical signal acquisition means can be performed with conjunction with invasive procedures (e.g., via surgery or invasive radiologic intervention protocols) or non-invasively (e.g., via imaging).

While the present disclosure is directed to the beneficial quantification of biophysical signal quality in the diagnosis and treatment of cardiac-related pathologies and conditions and/or neurological-related pathologies and conditions, such quantification can be applied to the diagnosis and treatment (including, surgical, minimally invasive, and/or pharmacologic treatment) of any pathologies or conditions in which a biophysical signal is involved in any relevant system of a living body. One example in the cardiac context is the diagnosis of CAD and its treatment by any number of therapies, alone or in combination, such as the placement of a stent in a coronary artery, performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other disease such as blood or other disorders), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

Skeletal-muscle-related signals (e.g., as characterized in electromyograms (EMG)) are often characterized as being "in-band noise" with respect to a cardiac signal, a neurological signal, etc.—that is, it often occurs in the same or similar frequency range within the acquired biophysical signal of interest. For example, for cardiac signals, the dominant frequency components of signals produced are often between about 0.5 Hz and about 80 Hz. For neurological signals such as brain signals, the frequency components are often between about 0.1 Hz and about 50 Hz. Also, depending on the degree of contamination, skeletal-muscle-related signals can also have a same, or similar, amplitude as typical cardiac-based waveforms and neurologic-based waveforms, etc. Indeed, similarity of skeletal-muscle-related signals to cardiac signals, neurologic and other biophysical signals, etc., can cause significant issues for the analysis of biophysical signals of interest. Therefore, quantifying the signal quality of a measured biophysical signal can be critical for, e.g., the quality assessment of acquired biophysical signals of interest and the rejection of contaminated acquired signals from being used in subsequent analyses, providing information useful in subsequent analyses to enable compensation for the contamination, etc.

The methods and systems described in the various embodiments herein are not so limited and may be utilized in any context of another physiological system or systems, organs, tissue, cells, etc. of a living body. By way of example only, two biophysical signal types that may be useful in the cardiovascular context include cardiac signals that may be acquired via conventional electrocardiogram (ECG/EKG) equipment, bipolar wide-band biopotential (cardiac) signals that may be acquired from other equipment such as those described herein, and signals that may be acquired by various plethysmographic techniques, such as, e.g., photoplethysmography.

In the context of the present disclosure, techniques for acquiring and analyzing biophysical signals are described in particular for use in diagnosing the presence, non-presence, localization (where applicable), and/or severity of certain disease states or conditions in, associated with, or affecting, the cardiovascular (or cardiac) system, including for example pulmonary hypertension (PH), coronary artery disease (CAD), and heart failure (e.g., left-side or right-side heart failure).

Pulmonary hypertension, heart failure, and coronary artery disease are three diseases/conditions affiliated with the cardiovascular or cardiac system. Pulmonary hypertension (PH) generally refers to high blood pressure in the arteries of the lungs and can include a spectrum of conditions. PH typically has a complex and multifactorial etiology and an insidious clinical onset with varying severity. PH may progress to complications such as right heart failure and in many cases is fatal. The World Health Organization (WHO) has classified PH into five groups or types. The first PH group classified by the WHO is pulmonary arterial hypertension (PAH). PAH is a chronic and currently incurable disease that, among other things, causes the walls of the arteries of the lungs to tighten and stiffen. PAH requires at a minimum a heart catheterization for diagnosis. PAH is characterized by vasculopathy of the pulmonary arteries and defined, at cardiac catheterization, as a mean pulmonary artery pressure of 25 mm Hg or more. One form of pulmonary arterial hypertension is known as idiopathic pulmonary arterial hypertension—PAH that occurs without a clear cause. Among others, subcategories of PAH include heritable PAH, drug and toxin induced PAH, and PAH associated with other systemic diseases such as, e.g., connective tissue disease, HIV infection, portal hypertension, and congenital heart disease. PAH includes all causes that lead to the structural narrowing of the pulmonary vessels. With PAH, progressive narrowing of the pulmonary arterial bed results from an imbalance of vasoactive mediators, including prostacyclin, nitric oxide, and endothelin-1. This leads to an increased right ventricular afterload, right heart failure, and premature death. The second PH group as classified by the WHO is pulmonary hypertension due to left heart disease. This group of disorders is generally characterized by problems with the left side of the heart. Such problems can, over time, lead to changes within the pulmonary arteries. Specific subgroups include left ventricular systolic dysfunction, left ventricular diastolic dysfunction, valvular disease and, finally, congenital cardiomyopathies and obstructions not due to valvular disease. Treatments of this second PH group tends to focus on the underlying problems (e.g., surgery to replace a heart valve, various medications, etc.). The third PH group as classified by the WHO is large and diverse, generally relating to lung disease or hypoxia. Subgroups include chronic obstructive pulmonary disease, interstitial lung disease, sleep breathing disorders, alveolar hypoventilation disorders, chronic high-altitude exposure, and developmental lung disease. The fourth PH group is classified by the WHO as chronic thromboembolic pulmonary hypertension, caused when blood clots enter or form within the lungs, blocking the flow of blood through the pulmonary arteries. The fifth PH group is classified by the WHO as including rare disorders that lead to PH, such as hematologic disorders, systemic disorders such as sarcoidosis that have lung involvement, metabolic disorders, and a subgroup of other diseases. The mechanisms of PH in this fifth group are poorly understood.

PH in all of its forms can be difficult to diagnose in a routine medical examination because the most common symptoms of PH (shortness of breath, fatigue, chest pain, edema, heart palpitations, dizziness) are associated with so many other conditions. Blood tests, chest x-rays, electro- and echocardiograms, pulmonary function tests, exercise tolerance tests, and nuclear scans are all used variously to help a physician to diagnose PH in its specific form. As noted above, the "gold standard" for diagnosing PH, and for PAH in particular, is a cardiac catherization of the right side of the heart by directly measuring the pressure in the pulmonary arteries. If PAH is suspected in a subject, one of several investigations may be performed to confirm the condition, such as electrocardiography, chest radiography, and pulmonary function tests, among others. Evidence of right heart strain on electrocardiography and prominent pulmonary arteries or cardiomegaly on chest radiography is typically seen. However, a normal electrocardiograph and chest radiograph cannot necessarily exclude a diagnosis of PAH. Further tests may be needed to confirm the diagnosis and to establish cause and severity. For example, blood tests, exercise tests, and overnight oximetry tests may be performed. Yet further, imaging testing may also be performed. Imaging testing examples include isotope perfusion lung scanning, high resolution computed tomography, computed tomography pulmonary angiography, and magnetic resonance pulmonary angiography. If these (and possibly other) non-invasive investigations support a diagnosis of PAH, right heart catheterization typically is needed to confirm the diagnosis by directly measuring pulmonary pressure. It also allows measurement of cardiac output and estimation of left atrial pressure using pulmonary arterial wedge pressure. While non-invasive techniques exist to determine whether PAH may exist in a subject, these techniques cannot reliably confirm a diagnosis of PAH unless an invasive right heart catherization is performed. Aspects and embodiments of methods and systems for assessing PH are disclosed in commonly-owned U.S. patent application Ser. No. 16/429, 593, the entirety of which is hereby incorporated by reference.

Heart failure affects almost 6 million people in the United States alone, and more than 870,000 people are diagnosed with heart failure each year. The term "heart failure" (sometimes referred to as congestive heart failure or CHF) generally refers to a chronic, progressive condition or process in which the heart muscle is unable to pump enough blood to meet the needs of the body, either because the heart muscle is weakened or stiff or because a defect is present that prevents proper circulation. This results in, e.g., blood and fluid backup into the lungs, edema, fatigue, dizziness, fainting, rapid and/or irregular heartbeat, dry cough, nausea and shortness of breath. Common causes of heart failure are coronary artery disease (CAD), high blood pressure, cardiomyopathy, arrhythmia, kidney disease, heart defects, obesity, tobacco use and diabetes. Diastolic heart failure (DHF), left- or left-sided heart failure/disease (also referred to as left ventricular heart failure), right- or right-sided heart failure/ disease (also referred to as right ventricular heart failure) and systolic heart failure (SHF) are common types of heart failure.

Left-sided heart failure is further classified into two main types: systolic failure (or heart failure with reduced ejection fraction or reduced left ventricular function) and diastolic failure/dysfunction (or heart failure with preserved ejection fraction or preserved left ventricular function). Procedures and technologies commonly used to determine if a patient has left-sided heart failure include cardiac catheterization, x-ray, echocardiogram, electrocardiogram (EKG), electrophysiology study, radionucleotide imaging, and various treadmill tests, including a test that measures peak $VO_2$. Ejection fraction (EF), which is a measurement expressed as a percentage of how much blood a ventricle pumps out with each contraction (and in the case of left-sided heart failure the left ventricle), is most often obtained non-invasively via an echocardiogram. A normal left ventricular ejection fraction (LVEF) ranges from about 55% to about 70%.

When systolic failure occurs, the left ventricle cannot contract forcefully enough to keep blood circulating normally throughout the body, which deprives the body of a normal supply of blood. As the left ventricle pumps harder to compensate, it grows weaker and thinner. As a result, blood flows backwards into organs, causing fluid buildup in the lungs and/or swelling in other parts of the body. Echocardiograms, magnetic resonance imaging, and nuclear medicine scans (e.g., multiple gated acquisition) are techniques used to noninvasively measure ejection fraction (EF), expressed as a percentage of the volume of blood pumped by the left ventricle relative to its filling volume to aid in the diagnosis of systolic failure. In particular, left ventricular ejection fraction (LVEF) values below 55% indicate the pumping ability of the heart is below normal, and can in severe cases be measured at less than about 35%. In general, a diagnosis of systolic failure can be made or aided when these LVEF values are below normal.

When diastolic heart failure occurs, the left ventricle has grown stiff or thick, losing its ability to relax normally, which in turn means that the lower left chamber of the heart is unable to properly fill with blood. This reduces the amount of blood pumped out to the body. Over time, this causes blood to build up inside the left atrium, and then in the lungs, leading to fluid congestion and symptoms of heart failure. In this case, LVEF values tend to be preserved within the normal range. As such, other tests, such as an invasive catheterization may be used to measure the left ventricular end diastolic pressure (LVEDP) to aid in the diagnosis of diastolic heart failure as well as other forms of heart failure with preserved EF. Typically, LVEDP is measured either directly by the placement of a catheter in the left ventricle or indirectly by placing a catheter in the pulmonary artery to measure the pulmonary capillary wedge pressure. Such catheterization techniques, by their nature, increase the risk of infection and other complications to the patient and tend to be costly. As such, non-invasive methods and systems for determining or estimating LVEDP in diagnosing the presence or non-presence and/or severity of diastolic heart failure as well as myriad other forms of heart failure with preserved EF are desirable. In addition, non-invasive methods and systems for diagnosing the presence or non-presence and/or severity of diastolic heart failure as well as myriad other forms of heart failure with preserved EF, without necessarily including a determination or estimate of an abnormal LVEDP, are desirable. Embodiments of the present disclosure address all of these needs.

Right-sided heart failure often occurs due to left-sided heart failure, when the weakened and/or stiff left ventricle loses power to efficiently pump blood to the rest of the body. As a result, fluid is forced back through the lungs, weakening the heart's right side, causing right-sided heart failure. This backward flow backs up in the veins, causing fluid to swell in the legs, ankles, GI tract and liver. In other cases, certain lung diseases such as chronic obstructive pulmonary disease and pulmonary fibrosis can cause right-sided heart failure, despite the left side of the heart functioning normally. Procedures and technologies commonly used to determine if a patient has left-sided heart failure include a blood test, cardiac CT scan, cardiac catheterization, x-ray, coronary angiography, echocardiogram, electrocardiogram (EKG), myocardial biopsy, pulmonary function studies, and various forms of stress tests such as a treadmill test.

Pulmonary hypertension is closely associated with heart failure. As noted above, PAH (the first WHO PH group) can lead to an increased right ventricular afterload, right heart failure, and premature death. PH due to left heart failure (the second WHO PH group) is believed to be the most common cause of PH.

Ischemic heart disease, also known as cardiac ischemia or myocardial ischemia, and related condition or pathologies may also be estimated or diagnosed with the techniques disclosed herein. Ischemic heart disease is a disease or group of diseases characterized by a reduced blood supply to the heart muscle, usually due to coronary artery disease (CAD). CAD is closely related to heart failure and is its most common cause. CAD typically occurs when the lining inside the coronary arteries that supply blood to the myocardium, or heart muscle, develops atherosclerosis (the hardening or stiffening of the lining and the accumulation of plaque therein, often accompanied by abnormal inflammation). Over time, CAD can also weaken the heart muscle and contribute to, e.g., angina, myocardial infarction (cardiac arrest), heart failure, and arrhythmia. An arrhythmia is an abnormal heart rhythm and can include any change from the normal sequence of electrical conduction of the heart and in some cases can lead to cardiac arrest. The evaluation of PH, heart failure, CAD and other diseases and/or conditions can be complex, and many invasive techniques and tools are used to assess the presence and severity of the conditions as noted above. In addition, the commonalities among symptoms of these diseases and/or conditions as well as the fundamental connection between the respiratory and cardiovascular systems—due to the fact that they work together to oxygenate the cells and tissues of the body—point to a complex physiological interrelatedness that may be exploited to improve the detection and ultimate treatment of such diseases and/or conditions. Conventional methodologies to assess these biophysical signals in this context still pose significant challenges in giving healthcare providers tools for accurately detecting/diagnosing the presence or non-presence of such diseases and conditions.

For example, in electrocardiography—a field of cardiology in which the heart's electrical activity is analyzed to obtain information about its structure and function—it has been observed that significant ischemic heart disease can alter ventricular conduction properties of the myocardium in the perfusion bed downstream of a coronary artery narrowing or occlusion, the pathology can express itself at different locations of the heart and at different stages of severity, making an accurate diagnosis challenging. Further, the electrical conduction characteristics of the myocardium may vary from person to person, and other factors such as measurement variability associated with the placement of measurement probes and parasitic losses associated with such probes and their related components can also affect the biophysical signals that are captured during electrophysiologic tests of the heart. Further still, when conduction properties of the myocardium are captured as relatively long cardiac phase gradient signals, they may exhibit complex nonlinear variability that cannot be efficiently captured by traditional modeling techniques.

In an aspect, a method is disclosed to acquire a biophysical-signal data set for clinical analysis (e.g., as part of a machine-learning data set or for clinical diagnostics), the method comprising: obtaining, by a processor, a biophysical-signal data set, or a portion thereof, of a subject for a measurement (e.g., of the subject's heart, brain, lungs, etc.), wherein the biophysical-signal data set, or the portion thereof, is acquired via one or more surface probes of a non-invasive measurement system (e.g., placed on the chest of the subject) over one or more corresponding channels and acquired for an acquisition duration suitable for subsequent assessment (e.g., greater than about 120 seconds, e.g., around about 210 seconds), wherein the acquisition duration is pre-defined, dynamically determined, or set by a user; determining, by the processor (e.g., of the non-invasive measurement system), one or more signal quality parameters of the obtained biophysical-signal data set, wherein at least one of the one or more signal quality parameters is selected from group consisting of powerline interference parameter associated with powerline noise contamination, a high-frequency noise parameter associated with high frequency noise contamination, a noise burst parameter associated with high frequency noise burst contamination, an abrupt movement parameter associated with abrupt movement contamination, and an asynchronous noise parameter associated with skeletal muscle contamination or heart cycle variability; and rejecting, by the processor, the obtained biophysical-signal data set, or the assessed portion thereof, when the one or more signal quality parameters fails a noise quality assessment performed on the one or more signal quality parameters (e.g., wherein the rejection causes the processor to output a visual indicator of the failed assessment at the non-invasive measurement system, an audio indicator of the failed assessment at the non-invasive measurement system, or a report of the failed assessment at the non-invasive measurement system, wherein the output is contemporaneous, or near contemporaneous, with the measurement) (e.g., wherein the rejection facilitates acquisition of a second biophysical-signal data set, or a portion thereof, of the subject immediately following the acquisition of the biophysical-signal) (e.g., wherein a non-rejection, or acceptance, assessment of the obtained biophysical-signal data set causes the processor to transmit, over a network, the obtained biophysical-signal data set for a remote clinical analysis).

In some embodiments, the method further includes outputting one or more of a visual indicator, an audio indicator, a vibratory indicator and a report of the failed assessment at the non-invasive measurement system, wherein the output is contemporaneous, or near contemporaneous, with the measurement (e.g., to facilitate acquisition of a second biophysical-signal data set, or a portion thereof, of the subject immediately following the acquisition of the biophysical signal).

In some embodiments, the method further includes transmitting, by the processor, over a network, the obtained biophysical-signal data set for a remote clinical analysis following a non-rejection, or acceptance, assessment of the obtained biophysical-signal data set.

In some embodiments, the method further includes acquiring, by one or more acquisition circuits of the measurement system, voltage gradient signals over the one or more channels, wherein the voltage gradient signals are acquired at a frequency greater than about 1 kHz; and generating, by the one or more acquisition circuits, the obtained biophysical data set from the acquired voltage gradient signals. In some embodiments, the method further comprises placing at least a first surface probe at a first axis of the subject that passes through a body of the subject from left to right; placing at least a second surface probe at a second axis of the subject that passes through the body of the subject from superior to inferior; and placing at least a third surface probe at a third axis that passes through the body of the subject from anterior to posterior, wherein the first axis, the second axis, and the third axis are mutually orthogonal axes.

In some embodiments, the obtained biophysical-signal data set, or the assessed portion thereof, is rejected when the powerline interference parameter for any of the one or more channels fails a powerline interference condition (e.g., exceeds a powerline interference threshold).

In some embodiments, the obtained biophysical-signal data set, or the assessed portion thereof, is rejected when the high frequency noise parameter associated with high frequency noise contamination for any of the one or more channels fails a high frequency noise condition (e.g., when a high frequency noise score exceeds a predetermined high frequency noise threshold).

In some embodiments, the obtained biophysical-signal data set, or the assessed portion thereof, is rejected when the noise burst parameter associated with high frequency noise burst contamination for any of the one or more channels fails a noise condition (e.g., using a high frequency time series to test one second windows and comparing the one second windows to a median high frequency energy, and rejecting the biophysical-signal data set when the one second energy is larger than twice the median).

In some embodiments, the obtained biophysical-signal data set, or the assessed portion thereof, is rejected when the abrupt movement parameter associated with abrupt movement contamination for any of the one or more channels fails an abrupt movement condition (e.g., when a baseline in a one second window of a signal changes relative to a previous window by more than 25% of the ventricular depolarization amplitude of the channel).

In some embodiments, the obtained biophysical-signal data set, or the assessed portion thereof, is rejected when the asynchronous noise parameter which can include skeletal muscle contamination or heart cycle variability for any of the one or more channels fails an asynchronous noise condition (e.g., when the cycle variability noise exceeds a predetermined threshold).

In some embodiments, a powerline coefficient is determined by: performing, by the processor, a Fourier transform (e.g., Fast Fourier transform) of the obtained biophysical-signal data set, or the portion thereof; and determining, by the processor, maximum powerline energy at a plurality of frequency ranges (e.g., at around 50 Hz, e.g., between about 48 Hz and about 52 Hz; at around 60 Hz, e.g., between about 58 Hz and about 62 Hz; at around 150 Hz. e.g., between about 145 Hz and about 155 Hz; at around 180 Hz, e.g., between about 175 Hz and about 185 Hz; and at around 300 Hz, e.g., between about 295 Hz and about 305 Hz).

In some embodiments, the assessment is a gating stage for subsequent analysis of the subject for coronary artery disease, pulmonary hypertension, or other pathologies or disease states.

In some embodiments, the received biophysical-signal data set comprises a cardiac signal data set.

In some embodiments, the biophysical-signal data set is generated in near real-time as biophysical signals are acquired.

In some embodiments, the biophysical signals are acquired from sensors in a smart device or in a handheld medical diagnostic equipment.

In some embodiments, the biophysical-signal data set comprises wide-band cardiac phase gradient cardiac signal data derived from biopotential signals simultaneously captured from a plurality of surface electrodes placed on surfaces of a body in proximity to a heart of the subject.

In another aspect, a method is disclosed of rejecting an acquired biophysical signal, the method comprising: receiving, by a processor, a biophysical-signal data set of a subject; comparing, by the processor, the received biophysical-signal data set to at least one of powerline interference, high frequency noise, high frequency noise bursts, abrupt baseline movement, and cycle variability; and rejecting, by the processor, the received biophysical-signal data set based on the comparison.

In some embodiments, comparing the received biophysical-signal data set to powerline interference comprises determining a powerline coefficient of the biophysical-signal data set, and wherein rejecting the received biophysical-signal data set comprises rejecting the biophysical-signal data set when the powerline coefficient exceeds a predetermined threshold.

In some embodiments, comparing the received biophysical-signal data set to high frequency noise comprises determining a high frequency noise score of the biophysical-signal data set, and wherein rejecting the received biophysical-signal data set comprises rejecting the biophysical-signal data set when the high frequency noise score exceeds a predetermined threshold.

In some embodiments, comparing the received biophysical-signal data set to high frequency noise bursts comprises determining high frequency noise bursts of the biophysical-signal data set using a high frequency time series to test one second windows and comparing the one second windows to a threshold, and wherein rejecting the received biophysical-signal data set comprises rejecting the biophysical-signal data set when the one second energy is larger than the threshold.

In some embodiments, comparing the received biophysical-signal data set to abrupt baseline movement comprises determining an abrupt movement in baseline when a baseline in a predetermined time window of a signal changes relative to a previous window by more than a predetermined amount, and wherein rejecting the received biophysical-signal data set comprises rejecting the biophysical-signal data set when the abrupt movement in baseline is determined.

In some embodiments, comparing the received biophysical-signal data set to cycle variability comprises determining a cycle variability noise, and wherein rejecting the received biophysical-signal data set comprises rejecting the biophysical-signal data set when the cycle variability noise exceeds a predetermined threshold.

In some embodiments, the comparison comprises determining presence of asynchronous noise present in the acquired biophysical-signal data set having a value or energy over a pre-defined threshold.

In some embodiments, the method further comprises generating, by the processor, a notification of a failed acquisition of biophysical-signal data set. In some embodiments, the notification prompts a subsequent acquisition of the biophysical-signal data set to be performed.

In some embodiments, the method further comprises causing, by the processor, transmission of the received biophysical-signal data set over a network to an external analysis system, wherein the analysis system is configured to analyze the received biophysical-signal data for presence, or degree, of a pathology or clinical condition.

In another aspect, a system is disclosed comprising: one or more processors; and a memory having instructions stored thereon, wherein execution of the instruction by the one or more processors cause the one or more processors to perform any one of the above-recited methods.

In another aspect, a non-transitory computer readable medium is disclosed, the computer readable medium having instructions stored thereon, wherein execution of the instruction by one or more processors cause the one or more processors to perform any one of the above-recited methods.

BRIEF DESCRIPTION OF THE DRAWINGS

The accompanying drawings, which are incorporated in and constitute a part of this specification, illustrate embodiments and together with the description, serve to explain the principles of the methods and systems contained herein. Embodiments may be better understood from the following detailed description when read in conjunction with the accompanying drawings. The drawings include the following figures.

DETAILED SPECIFICATION

Each and every feature described herein, and each and every combination of two or more of such features, is included within the scope of the present invention provided that the features included in such a combination are not mutually inconsistent.

As described further herein, the signal quality of an acquired signal is assessed in real-time and a notification is generated and provided to the attending technician if the acquired signal is corrupted by noise. In one or more implementations, the assessment includes: (1) detection of powerline interference; (2) detection of abrupt movement; (3) detection of noise burst; (4) confirmation of minimum signal-to-noise ratio (SNR); and/or (5) detection of asynchronous noise (e.g., electromyography (EMG) noise).

As described further herein, a signal is acquired and a determination is made in real time if there is a problem with the acquisition (e.g., the acquired signal is processed immediately to determine if the acquired signal is acceptable or unacceptable, is of sufficient quality for subsequent assessment, etc.); if there is a problem, output is provided to indicate that signal acquisition needs to be performed again (i.e., if the acquired signal is unacceptable, reject the acquired signal).

Figure 1A:
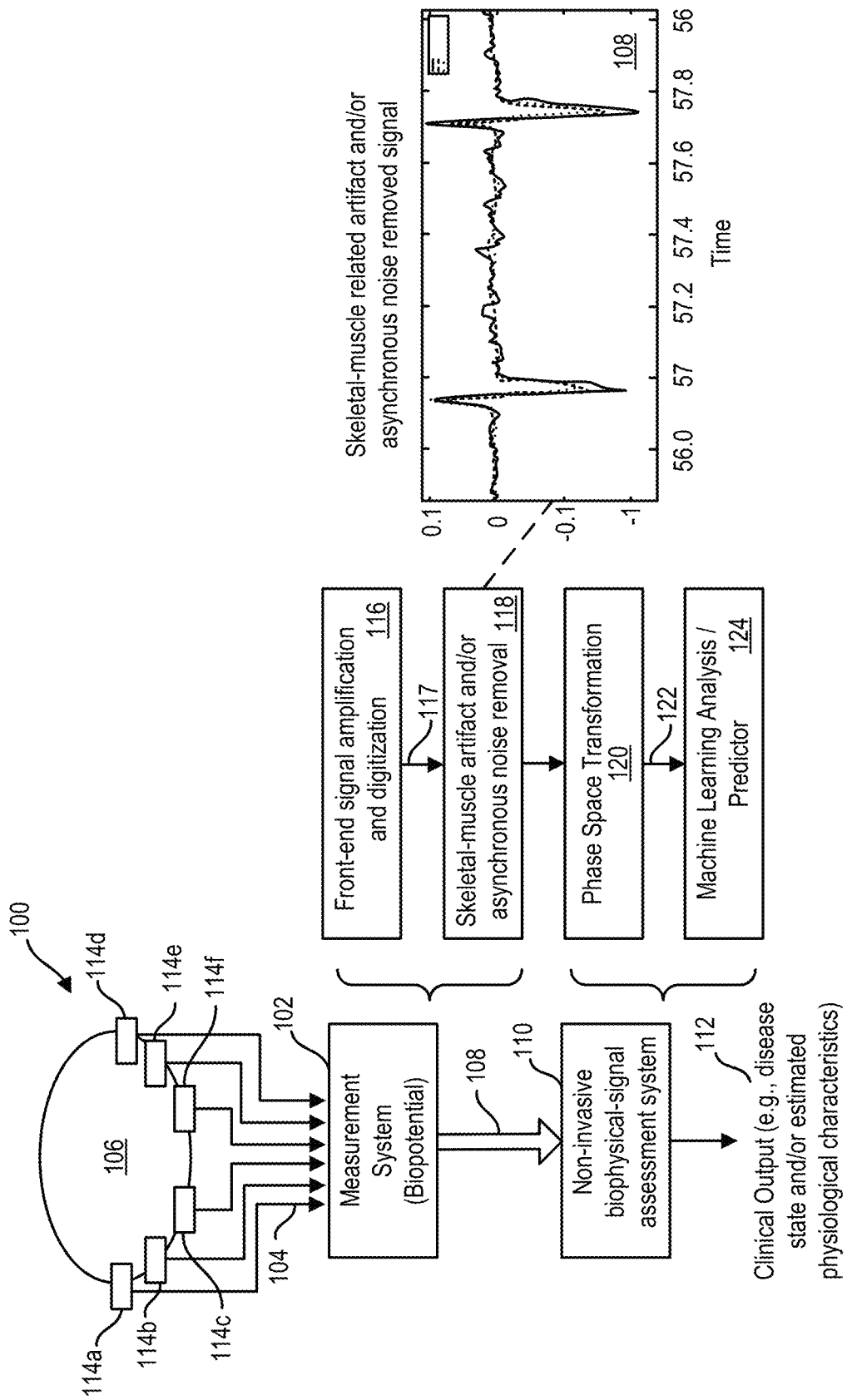
FIG. 1A is a diagram of an example system configured to quantify and remove asynchronous noise and artifact contamination to more accurately assess complex nonlinear variabilities in quasi-periodic systems, such as biological systems having biophysical signals, in accordance with an illustrative embodiment.

FIG. 1A is a diagram of an example system 100 configured to quantify and remove asynchronous noise such as skeletal-muscle-related artifact noise contamination and using such quantification to more accurately assess complex nonlinear variabilities in quasi-periodic systems, in accordance with an illustrative embodiment. As used herein, the term "remove", and other like terms, refers to any meaningful reduction, in whole or in part, in noise contamination that improves or benefits subsequent analysis.

In FIG. 1A, measurement system 102 is a non-invasive embodiment (shown as "Measurement System (biophysical)" 102) that acquires a plurality of biophysical signals 104 via any number of measurement probes 114 (shown in the system 100 of FIG. 1 as including six such probes 114*a*, 114*b*, 114*c*, 114*d*, 114*e*, and 114*f*) from a subject 106 to produce a biophysical-signal data set 108 that is made available to a non-invasive biophysical-signal assessment system 110 to determine a clinical output 112. In some embodiments, the clinical output includes an assessment of the presence or non-presence of a disease and/or an estimated physiological characteristic of the physiological system under study. In other embodiments, there is no clinical output but rather output of information that may be used by a clinician to provide their own clinical assessment of the information relative to the patient whose signals are being assessed.

In some embodiments, and as shown in FIG. 1A, measurement system 102 is configured to remove asynchronous noise contamination (e.g., via operation 118) from the amplified and digitized biophysical-signal data set 117 that has been processed/conditioned by a front-end amplification and digitization operation 116. The noise contamination removal operation 118 is based on a quantification of the asynchronous noise potentially present in the digitized biophysical-signal data set 117. The operation 118, in some embodiments of removing asynchronous noise could be performed in near real time, e.g., via a processor and corresponding instructions or via digital circuitries (e.g., CPLD, microcontroller, and the like), once a representative cycle data set is established, e.g., from a few samples of the acquired biophysical-signal data set 108. Acquired biophysical-signal data set 108 refers to any data set (e.g., 117, 108) generated by, or within, the measurement system 102 following the front-end amplification and digitization operation 116. In some embodiments, a few hundred samples can be used to establish a representative cycle data set. In other embodiments, a few thousand samples can be used to establish a representative cycle data set. In some embodiments, the quantification of the asynchronous noise is performed in hardware circuits that are integrated into, and operate with, the front-end amplification and digitization operation 116.

Measurement system 102, in some embodiments, is configured to acquire biophysical signals that may be based on the body's biopotential via biopotential sensing circuitries as biopotential biophysical signals. In the cardiac and/or electrocardiography contexts, measurement system 102 is configured to capture cardiac-related biopotential or electrophysiological signals of a living subject (such as a human) as a biopotential cardiac signal data set. In some embodiments, measurement system 102 is configured to acquire a wide-band cardiac phase gradient signals as a biopotential signal or other signal types (e.g., a current signal, an impedance signal, a magnetic signal, an optical signal, an ultrasound or acoustic signal, etc.). The term "wide-band" in reference to an acquired signal, and its corresponding data set, refers to the signal having a frequency range that is substantially greater than the Nyquist sampling rate of the highest dominant frequency of a physiological system of interest. For cardiac signals, which typically has a dominant frequency components between about 0.5 Hz and about 80 Hz, the wide-band cardiac phase gradient signals or wide-band cardiac biophysical signals comprise cardiac frequency information at a frequency selected from the group consisting between about 0.1 Hz and about 1 KHz, between about 0.1 Hz and about 2 KHz, between about 0.1 Hz and about 3 KHz, between about 0.1 Hz and about 4 KHz, between about 0.1 Hz and about 5 KHz, between about 0.1 Hz and about 6 KHz, between about 0.1 Hz and about 7 KHz, between about 0.1 Hz and about 8 KHz, between about 0.1 Hz and about 9 KHz, between about 0.1 Hz and about 10 KHz, and between about 0.1 Hz and greater than 10 KHz (e.g., 0.1 Hz to 50 KHz or 0.1 Hz to 500 KHz). In addition to capturing the dominant frequency components, the wide-band acquisition also facilitate capture of other frequencies of interest. Examples of such frequencies of interest can include QRS frequency profiles (which can have frequency ranges up to 250 Hz), among others. The term "phase gradient" in reference to an acquired signal, and corresponding data set, refers to the signal being acquired at different vantage points of the body to observe phase information for a set of distinct events/functions of the physiological system of interest. Following the signal acquisition, the term "phase gradient" refers to the preservation of phase information via use of non-distorting signal processing and pre-processing hardware, software, and techniques (e.g., phase-linear filters and signal-processing operators and/or algorithms).

In the neurological context, measurement system 102 is configured to capture neurological-related biopotential or electrophysiological signals of a living subject (such as a human) as a neurological biophysical signal data set. In some embodiments, measurement system 102 is configured to acquire wide-band neurological phase gradient signals as a biopotential signal or other signal types (e.g., a current signal, an impedance signal, a magnetic signal, an ultrasound, an optical signal, an ultrasound or acoustic signal, etc.). Examples of measurement system 102 are described in U.S. Publication No. 2017/0119272 and in U.S. Publication No. 2018/0249960, each of which is incorporated by reference herein in its entirety.

In some embodiments, measurement system 102 is configured to capture wide-band biopotential biophysical phase gradient signals as unfiltered electrophysiological signals such that the spectral component(s) of the signals are not altered. Indeed, in such embodiments, the wide-band biopotential biophysical phase gradient signals are captured, converted, and even analyzed without having been filtered (via, e.g., hardware circuitry and/or digital signal processing techniques, etc.) (e.g., prior to digitization) that otherwise can affect the phase linearity of the biophysical signal of interest. In some embodiments, the wide-band biopotential biophysical phase gradient signals are captured in microvolt or sub-microvolt resolutions that are at, or significantly below, the noise floor of conventional electrocardiographic, electroencephalographic, and other biophysical-signal acquisition instruments. In some embodiments, the wide-band biopotential biophysical signals are simultaneously sampled having a temporal skew or "lag" of less than about 1 microseconds, and in other embodiments, having a temporal skew or lag of not more than about 10 femtoseconds. Notably, the exemplified system minimizes non-linear distortions (e.g., those that can be introduced via certain filters) in the acquired wide-band phase gradient signal to not affect the information therein.

Referring still to FIG. 1A, assessment system 110 is configured to receive over, e.g., a network, the acquired biophysical-signal data set 108 (that in this embodiment has been denoised) and to, in some embodiments, generate by a transformation operation 120 (labeled as "phase space transformation" 120) one or more three-dimensional vectorcardiogram data sets 122 for analysis via, e.g., one or more machine learning analysis operations and/or one or more predictor operations (shown as step 124) of the phase-gradient biophysical-signal data set 108. Examples of the transformation operation and the machine learning/predictor operation are discussed below as well as in U.S. Publication No. 2013/0096394, which is incorporated by reference herein in its entirety. In some embodiments, the acquired biophysical-signal data set 108 is structured as a multidimensional data set for subsequent processing without having to be explicitly transformed; e.g., where the intermediate data set is not visualized.

Figure 1B:
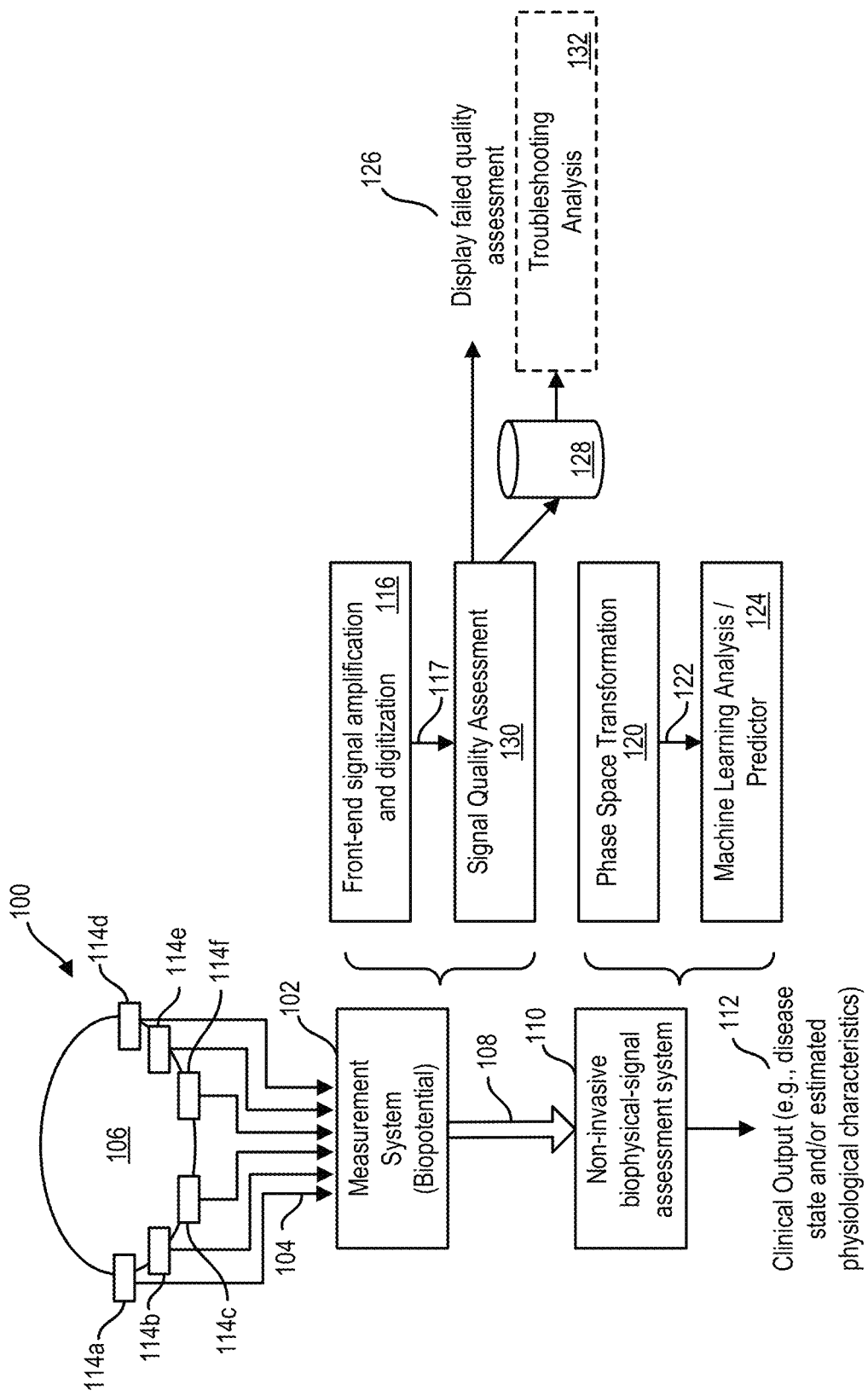
FIG. 1B is a diagram of an example system configured to reject an acquired biophysical signal based on a quantification of asynchronous noise and artifact contamination, in accordance with another illustrative embodiment.

In some embodiments, measurement system 102 is configured to assess the signal quality of the acquired biophysical signal and to reject some or all of the acquired signal data set based on such assessment. FIG. 1B is a diagram of an example system configured to reject an acquired biophysical signal based on an assessment of the acquired biophysical signal quality by quantification of asynchronous noise and artifact contamination, in accordance with another illustrative embodiment. In some embodiments, measurement system 102 is configured to perform the asynchronous noise removal operation 118 and the signal quality assessment operation 130 based on the quantification of the asynchronous noise.

Because a clinical analysis of the acquired biophysical signal data set 108 can be performed, in some embodiments, on a system that is separate (e.g., assessment system 110) from the measurement system 102, a signal quality check ensures that the acquired biophysical-signal data set 108 is suitable for subsequent clinical analysis. The operation may facilitate the prompting of the re-acquisition of the biophysical-signal data set by the non-invasive measurement system 102, thus ensuring that the acquired biophysical-signal data set is not contaminated by asynchronous noise (such as skeletal-muscle-related noise) prior to the biophysical-signal data set being subjected, or made available, to further processing and analysis for a clinical assessment.

In some embodiments, signal quality assessment operation 130 is performed in near real-time; e.g., in less than about 1 minute or less than about 5 minutes, in response to which system 102 can prompt for the re-acquisition of the biophysical-signal data set. This near real-time assessment allows the re-acquisition of the biophysical-signal data set, if desired, prior to the patient leaving the testing room or other location where the biophysical signal is being acquired. The analysis performed by assessment system 110 to determine a clinical output, in some embodiments, takes about 10-15 minutes to be performed. In other embodiments, this analysis takes less than about 5 minutes to be performed. In yet other embodiments, this analysis takes about 5-10 minutes to be performed. In still other embodiments this analysis takes more than about 15 minutes to be performed.

In some embodiments, the signal assessment is performed entirely in the same physical location as that of the patient (e.g., on one or more computing and/or storage devices located in the patient's bedroom or a clinician examination room). In some embodiments, the signal assessment is performed entirely in a different physical location from that of the patient (e.g., on one or more computing and/or storage devices located in another room, another building, another state, another country, etc.). In some embodiments, the signal assessment is performed in a networked environment involving multiple physical locations and multiple computing and/or storage devices. Such a networked environment can be secured to protect the privacy of the patient whose signals are being assessed to, e.g., comply with various privacy requirements.

In some embodiments, the signal assessment is performed as the signals are being acquired from the patient—e.g., as quickly or nearly as quickly as the signal assessment system is capable of operating (e.g., in real time or near-real time, depending on the signal assessment system configuration, network constraints, etc.). In other embodiments, the signal assessment is performed partially as the signals are acquired and partially after they have been acquired from the patient and stored. In still other embodiments, none of the signals are assessed as they are being acquired from the patient and instead are stored for assessment at a later time relative to the time they are acquired from the patient. Of course, all signals, regardless of the time they may be assessed, may be stored after being acquired for later assessment or reassessment.

One or more clinicians may perform a clinical assessment of the patient based in whole or in part on that patient's signal assessment performed by the systems and via methods described herein. Such clinicians may physically be with the patient and/or at a location physically removed from the patient. The signal assessment systems described herein can also perform, in whole or in part, a clinical assessment of the patient, by way, e.g., of a clinical output of an operation or operations performed by a signal assessment system. Alternatively, the signal assessment system may simply provide information that falls short of a clinical assessment for use by clinicians in performing their own clinical assessment of the patient. And in the case where the signal assessment system does provide a clinical output, the clinician may, as well, choose to accept or reject such clinical output in performing their own ultimate clinical assessment of the patient, in cases, for example, where such clinician involvement and ultimate decision making is desired or even required (by, e.g., law, protocol, insurance requirements, etc.).

In some embodiments, non-invasive measurement system 102 is configured to generate a notification 126 (labeled in FIG. 1B as "Display failed signal quality assessment" 126) of a failed or unsuitable acquisition of biophysical-signal data set, wherein the notification may also prompt the re-acquisition of biophysical-signals. The notification may be in any form; e.g., a visual output (e.g., one or more indicator lights or indicator on a screen), an audio output, a tactile/vibrational output (or any combination thereof) that is provided to a technician or clinician and/or to the patient. Examples of the user interface (e.g., graphical user interface) of the measurement system 102, for example, at which the notification 126 can be presented is provided in U.S. Publication No. 2017/0119272, filed Aug. 26, 2016, title "Method and Apparatus for Wide-Band Phase Gradient Signal Acquisition"; U.S. Design Application No. 29/578, 421, title "Display with Graphical User Interface, each of which is incorporated by reference herein in its entirety. To this end, all or a portion of the rejected biophysical-signal data set may not be used in subsequent analysis (e.g., 120, 124) to yield the clinical output 112.

In some embodiments, the rejected biophysical-signal data set optionally may be stored into any suitable memory (128) for further (troubleshooting) analysis (132) of defects and/or other reasons that led to the rejection of the acquired signal. To this end, all or a portion of the rejected biophysical-signal data set may not be used in subsequent analysis (e.g., 120, 124) to yield the clinical output 112, depending on the outcome of any such analysis 132.

In some embodiments, system 200 may use all or a portion of the rejected biophysical-signal data set in subsequent analysis (e.g., 120, 124) to yield the clinical output 112 or, e.g., to improve system 200 operational capability, etc.

In other embodiments, a clinician or other operator may control, alone or in connection with or as aided by system 200, whether and how all or a portion of the rejected biophysical signal data set may or may not be used.

Figure 2:
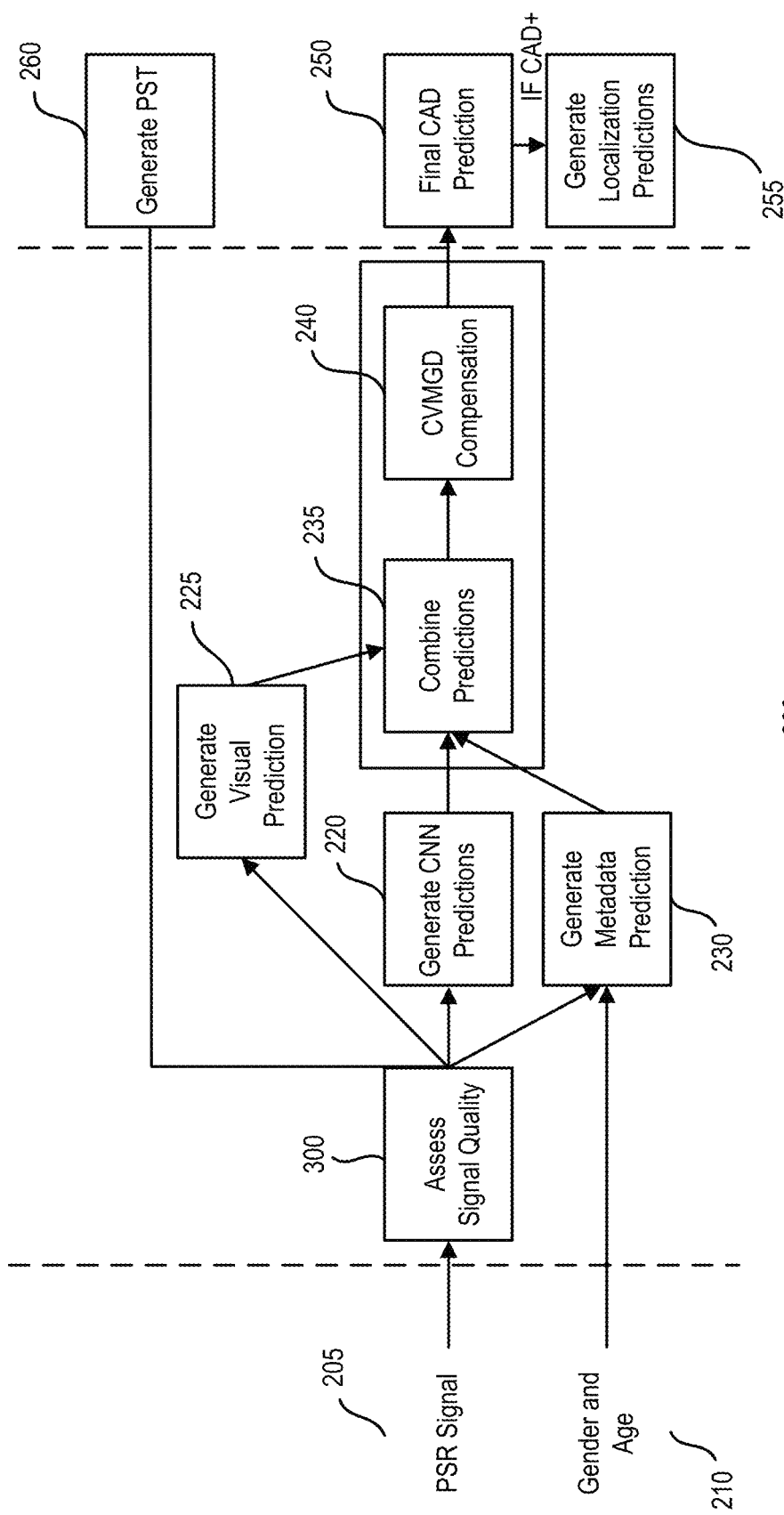
FIG. 2 is a diagram of an example assessment system in accordance with an illustrative embodiment.

FIG. 2 is a diagram of an example assessment system 200 in accordance with an illustrative embodiment. In system 200, different components of a coronary artery disease (CAD) assessment algorithm are assembled to provide an assessment of CAD. This begins with signal acceptance and ends with returning a final assessment of CAD, localization of that CAD to the affected artery(ies) and/or a set of one or more phase space tomographic dataset/images (also referred to as "PST data set/images"). Thus, system 200 may be used in determining, e.g., whether there is a lesion in any of the subject's coronary arteries. A CAD localization assessment may also be provided, e.g., if coronary disease is determined, and its presence may be localized to the appropriate coronary artery, such as the left circumflex artery (LCX), the left anterior descending artery (LAD), the right coronary artery (RCA), other arteries, or some combination thereof. Additionally, a PST data set/image; e.g., a two- or three-dimensional graphical representation of the assessment, may be generated and outputted via a phase space analysis.

Examples of useful phase space concepts and analysis are described in U.S. Publication No. 2018/0000371, title "Non-invasive Method and System for Measuring Myocardial Ischemia, Stenosis Identification, Localization and Fractional Flow Reserve Estimation"; U.S. Publication No. 2019/0214137, entitled "Method and System to Assess Disease Using Phase Space Volumetric Objects," filed Dec. 26, 2018; U.S. Publication No. 2019/0200893, entitled "Method and System to Assess Disease Using Phase Space Tomography and Machine Learning," each of which is incorporated by reference.

In some embodiments, system 200 includes a healthcare provider portal (also referred to herein as "Portal") configured to display stored phase space data set/images and/or clinical output 112 such as assessments of presence and/or non-presence of a disease and/or an estimated physiological characteristic of the physiological system under study (among other intermediate data sets) in a phase space analysis and/or angiographic-equivalent report. Healthcare provider portal, which in some embodiments may be termed a physician or clinician portal, is configured to access, retrieve, and/or display or present reports and/or the phase space volumetric data set/images and/or the clinical output 112 (and other data) for the report) from a repository (e.g., a storage area network).

In some embodiments, the healthcare provider portal is configured to display the phase space volumetric data set/images (or intermediate data set derived therefrom) and/or clinical output 112 in, or along with, an anatomical mapping report, a coronary tree report, and/or a 17-segment report. Healthcare provider portal may present the data, e.g., in real-time (e.g., as a web object), as an electronic document, and/or in other standardized or non-standardized data set visualization/image visualization/medical data visualization/scientific data visualization formats. The healthcare provider portal, in some embodiments, is configured to access and retrieve reports or the phase space volumetric data set/images or clinical output (and other data) for the report) from a repository (e.g., a storage area network). The healthcare provider portal and/or repository can be compliant with patient information and other personal data privacy laws and regulations (such as, e.g., the U.S. Health Insurance Portability and Accountability Act of 1996 and the EU General Data Protection Regulation) and laws relating to the marketing of medical devices (such as, e.g., the US Federal Food and Drug Act and the EU Medical Device Regulation). Further description of an example healthcare provider portal is provided in U.S. Publication No. 2018/0078146, title "Method and System for Visualization of Heart Tissue at Risk", which is incorporated by reference herein in its entirety. Although in certain embodiments, the healthcare provider portal is configured for presentation of patient medical information to healthcare professionals, in other embodiments, the healthcare provider portal can be made accessible to patients, researchers, academics, and/or other portal users.

The anatomical mapping report, in some embodiments, includes one or more depictions of a rotatable and optionally scalable three-dimensional anatomical map of cardiac regions of affected myocardium. The anatomical mapping report, in some embodiments, is configured to display and switch between a set of one or more three-dimensional views and/or a set of two-dimensional views of a model having identified regions of myocardium. The coronary tree report, in some embodiments, includes one or more two-dimensional view of the major coronary artery. The 17-segment report, in some embodiments, includes one or more two-dimensional 17-segment views of corresponding regions of myocardium. In each of the report, the value that indicates presence of cardiac disease or condition at a location in the myocardium, as well as a label indicating presence of cardiac disease, may be rendered as both static and dynamic visualization elements that indicates area of predicted blockage, for example, with color highlights of a region of affected myocardium and with an animation sequence that highlight region of affected coronary arter(ies). In some embodiments, each of the report includes textual label to indicate presence or non-presence of cardiac disease (e.g., presence of significant coronary artery disease) as well as a textual label to indicate presence (i.e., location) of the cardiac disease in a given coronary artery disease.

In the context of cardiovascular systems, in some embodiments, the healthcare provider portal (and corresponding user interface) is configured to present summary information visualizations of myocardial tissue that identifies myocardium at risk and/or coronary arteries that are blocked. The user interface can be a graphical user interface ("GUI") with a touch- or pre-touch sensitive screen with input capability. The user interface can be used, for example, to direct diagnostics and treatment of a patient and/or to assess patients in a study. The visualizations, for a given report of a study, may include multiple depictions of a rotatable three-dimensional anatomical map of cardiac regions of affected myocardium, a corresponding two-dimensional view of the major coronary arteries, and a corresponding two-dimensional 17-segment view of the major coronary arteries to facilitate interpretation and assessment of architectural features of the myocardium for characterizing abnormalities in the heart and in cardiovascular functions.

In the embodiment shown in FIG. 2, execution of assessment system 200 is gated at its initiation by the requirement that the signal be of sufficient quality for subsequent assessment, as described further in some embodiments. In other embodiments of system 200, this signal quality requirement may be optional (e.g., selectively activated by system 200 and/or a user) or not be present at all.

In system 200, a phase signal recorder (PSR) signal 205 along with data indicating the gender and/or age of the subject 210 (e.g., the patient) may be received as inputs. In an embodiment, PSR signal 205 (and its corresponding data set) is an unmodified signal that is an example of a wide-band phase gradient biophysical signal. In a specific implementation, data (pertaining to signal 205) from three channels dubbed "ORTH1", "ORTH2", and "ORTH3" are parsed out of a PSR file downloaded from a storage area network (e.g., referred to as a "phase signal data repository" (PSDR)). As schematically shown in FIG. 1A and FIG. 1B, a set of six probes or electrodes (e.g., probes 114a-114f) are positioned on subject 106. These electrodes 114 may be, e.g., arranged along three orthogonal axes of a subject's body. In an implementation, data from channel "ORTH1" corresponds to a bipolar acquisition channel data series that is recorded by the phase space recorder from electrodes 114 that are placed along or near one of these orthogonal axes of a subject that passes through the subject's body from a left side to a right side of the subject. Data from channel "ORTH2" corresponds to a second bipolar acquisition channel data series that is recorded by the phase space recorder from two other electrodes 114 that are placed along or near the second of these orthogonal axes that passes through the subject's body in the superior side to the inferior side of the subject. And data from channel "ORTH3" corresponds to a third bipolar acquisition channel data series that is recorded by the phase space recorder from two further electrodes 114 that are placed along or near the third of these orthogonal axes that passes through the subject's body in the anterior direction to the posterior direction. Signals of ORTH1, ORTH2, and ORTH3, and their corresponding data sets, can be arranged, e.g., in phase space coordinates, in mutually orthogonal axes. It is noted that ORTH1, ORTH2, and ORTH3 signals (e.g., as an example of wide-band phase-gradient biophysical signals) are referenced in some embodiments to more clearly distinguish from a vectorcardiography device.

Assess signal quality system module 300, described further in some embodiments with respect to FIGS. 3-21, and which may be comprised within the measurement system 102 of FIG. 1, e.g., to perform operation 130, assesses the input signal 383 (such as the PSR signal 205) to determine whether subsequent processing may proceed, or whether the signal is unacceptable (e.g., too noisy) and another input signal is to be acquired before subsequent processing may proceed. Thus, in the embodiment shown, the output of the assess signal quality system module 300 is an assessment of whether or not to proceed with further analysis (e.g., performed by intermediate processing components 220-240 as seen in FIG. 2) and a determination of the time window of the signal that is suitable for analysis. If the assessment indicates that, e.g., the acquired PSR signal 205 is so suitable (i.e., acceptable), then the PSR signal, its corresponding data set, and the determined time window are provided for subsequent processing by the intermediate processing components; otherwise, the assess signal quality system module 300 indicates (e.g., to a user) that the acquired PSR signal (e.g., signal 205) is unsuitable (i.e., unacceptable) and another PSR signal must be acquired for subsequent processing to proceed. As discussed above, in other embodiments, an unacceptable signal quality indication rendered by module 300 may be overridden by system 200 and/or a user and some or all of the input signal 383 may be used in subsequent processing. In addition, whether or not all or a part of the input signal 383 is used in connection with the assess signal quality system module 300, such signal 383 optionally may be stored into memory for analysis and/or future use, in whole or in part.

The intermediate processing components in the FIG. 2 embodiment comprise a Generate CNN (convolutional neural network) Predictions module 220, a Generate Visual Prediction module 225, a Generate Metadata Prediction module 230, a Combine Predictions module 235, and a CVMGD (cycle variability-mediated gender-dependent) Compensation module 240. Some of all of these intermediate processing components or modules may be present or absent in other configurations of system 200 as contemplated in other embodiments.

Generate CNN Predictions module 220 receives as an input, from the Assess Signal Quality module 300, the unmodified PSR signal 205 (channel data from ORTH1 and ORTH3 as parsed out of the PSR file downloaded from the PSDR) and the time window of the signal that is suitable for analysis. The output of the Generate CNN Predictions module 220 is an overall CAD assessment using, e.g., a weighted sum of two individual CNN models, such as $CNNModel_{129}$ and $CNNModel_{85}$, in one exemplary implementation. Other embodiments of system 200 contemplate the use of one CNN or more than two CNNs.

Generate Visual Prediction module 225 receives as an input from the Assess Signal Quality 300 the unmodified PSR signal 205 (channel data from ORTH1, ORTH2, and ORTH3 as parsed out of the PSR file downloaded from the PSDR), and outputs an overall CAD assessment through the extraction of visual features and application of a linear formula across those visual features (referred to below as "Visual Features Assessment").

Generate Metadata Prediction module 230 receives as input from the Assess Signal Quality module 300 the unmodified PSR signal 205. Module 230 also receives as input data 210 relating to or indicating the subject's gender (i.e., biological sex) and/or age. Module 230 outputs an overall CAD assessment of the subject through the use of a linear formula taking the gender and/or age data into account (referred to in the exemplary equations below as a "metadata").

In the FIG. 2 embodiment, Combine Predictions module 235 receives as input the overall CAD assessment from the Generate CNN Predictions module 220, the overall CAD assessment from the Generate Visual Prediction module 225, and the overall CAD assessment from the Generate Metadata Prediction module 230.

The output from the Combine Predictions module 235 comprises an intermediate continuous (non-binary) overall CAD assessment (referred to in the exemplary equations below as the "Intermediate CAD Assessment"). Details of how Combine predictions Module 235 may operate are provided below.

Z-score normalization is a statistical technique that centers a distribution at zero and scales the distribution to have a standard deviation of one, with the output from this process referred to as the "z-score". As used in some embodiments, z-score normalization is used to ensure that assessments (e.g., from 220, 225, 230) are comparable (e.g., each possesses the same mean and standard deviation) such that they not only may be combined with an averaging operation, but such that one or more assessments will not influence the other or others in an undesired way (e.g., dominate) when all assessments are combined—such that each assessment is evenly weighted and/or distributed. In other embodiments, z-score normalization may be modified, used differently or in connection with additional processing, not used at all, or replaced in whole by one or more other techniques to give, e.g., preferential weight and/or distribution of one or more assessments as desired.

In an implementation, the "Combined CNN Assessment" (already in this example as a weighted sum of two individual CNNs models, $CNNModel_{129}$ and $CNNModel_{85}$) from component 220 is added to the output of component/module 230 overall CAD (metadata) assessment with a weight of one to three (CNN to metadata), as shown in Equation 1. The resultant combined CNN assessment (Equation 1) is then normalized by removing a pre-computed constant, representing the mean of the N=411 Stage I PSR test set ("N=411_CNN_Mean"), and this normalized value is divided by a second pre-computed constant that represents the standard deviation of that same set ("N=411_CNN_SD"); the result of performing these two operations is the z-score of the combined CNN assessment, as shown in Equation 2.

$$\text{Combined } CNN \text{ Assessment} = (CNNModel_{129} \times 1) + \quad \text{(Equation 1)}$$
$$(CNNModel_{85} \times 2)] + (metadata \times 3)$$

$$Zscore_{Combined\,CNN\,Assessment} = \frac{\text{Combined } CNN \text{ Assessment} - \text{``}N = 411\_CNN\_Mean\text{''}}{\text{``}N = 411\_CNN\_SD\text{''}} \quad \text{(Equation 2)}$$

The CAD assessment outputted by the Generate Visual Prediction module 225 in this implementation is merged with the CAD assessment outputted by the Generate Metadata Prediction component 230 such that the average of these outputs is used for females (Equation 3) but only the output of the Metadata Prediction module 230 is used for males (Equation 4). The female and male "Visual Feature Assessment" values are then merged; e.g., via a set of union operator ∪ (per Equation 5) to provide a new set comprising the members of the first female set and the second male set. These merged values are then normalized by removing a pre-computed constant that represents the mean visual feature assessment of the N=411 Stage I PSR test set ("N=411_VF_Mean"). The resulting normalized values are then divided by a second pre-computed constant that represents the standard deviation of that same set ("N=411_VF_SD"). The result of performing these two operations is the z-score as shown in Equation 6.

$$\text{Visual Feature } Assessment_{Female} = \frac{(\text{Visual Feature Assessment} + metadata)}{2} \quad \text{(Equation 3)}$$

$$\text{Visual Feature } Assessment_{Male} = metadata \quad \text{(Equation 4)}$$

$$\text{Visual Feature } Assessment_{Female \cup Male} = \quad \text{(Equation 5)}$$
$$\text{Visual Feature } Assessment_{female} \cup$$
$$\text{Visual Feature } Assessment_{male}$$

$$Zscore_{Visual\,feature\,assessment} = \quad \text{(Equation 6)}$$
$$\frac{\text{Visual Feature } Assessment_{Female \cup Male} - \text{``}N = 411\_VF\_Mean\text{''}}{\text{``}N = 411\_VF\_SD\text{''}}$$

Continuing with this exemplary implementation of an embodiment, the outputs from the CNN Assessment (i.e., z-score per equation 2) and the Visual Feature Assessment (i.e., z-score per equation 6) are then averaged to create the "Intermediate CAD Assessment" value as the final output from the Combine Predictions component 235, as shown in Equation 7. In other words, module 235 sums, for each patient, the output of these z-scores and then divides that sum by two:

$$\text{Intermediate } CAD \text{ Assessment} = \frac{Zscore_{Visual\,feature\,assessment} + Zscore_{Combined\,CNN\,Assessment}}{2} \quad \text{(Equation 7)}$$

Continuing with this implementation of an embodiment, the CVMGD Compensation module 240 receives as input both the subject's gender and/or age data 210 and the Intermediate CAD Assessment output from the Combine Predictions module 235, and outputs a final continuous (non-binary) CAD assessment value that may be referred to as "final continuous CAD assessment". Component 240 utilizes the concept of a cycle variability score and calculates a maximum variability score for ORTH1 and ORTH3 (and, in some embodiments, for ORTH2). This cycle variability score captures information on changes between cardiac cycles, and, within a given range of that score, captures electrophysiological variability that embeds information content on the CAD status which is observed to be particularly applicable for male subjects. The compensation operation implemented in module 240 leverages that cycle variability information for male subject to improve overall disease assessment (e.g., as provided through the visual feature assessment and machine learned assessment). Indeed, the CVMGD Compensation module 240 operates with the underlying basis that within a given range of cycle variability, a positive CAD assessment for male subjects as outputted from the combine predictions component 235 is more likely to actually be a negative CAD assessment, and conversely, a negative CAD assessment as generated by the Combine Predictions component 235 for male subjects is more likely to be a CAD positive assessment.

In some embodiments, the CVMGD Compensation module 240 is configured to determine if both (i) the cycle variability score of a male subject (e.g., calculated by module 300) is within a pre-defined range (e.g., between 0.0071 and 0.0079) and (ii) the Intermediate CAD Assessment value for a given male subject as outputted by module 235 is greater than or equal to a pre-defined "threshold value" (e.g., stored within module 240) by an amount X. If both conditions are met (e.g., for a positive CAD assessment for the male subject having a certain cycle variability signature), the CVMGD Compensation module 240 is configured to determine the final continuous CAD assessment value for a male subject output the final continuous CAD assessment score as the threshold value minus the amount X (i.e., to provide a negative CAD assessment) in which X is determined as threshold value minus the difference between the intermediate CAD assessment score and the threshold value. That is, the CVMGD Compensation module adjusts the Intermediate CAD Assessment value determined via Equation 7 to a magnitude value equivalent to, or same as, the threshold value minus X. Conversely, the CVMGD Compensation module 240 is configured to determine if both (i) the cycle variability score of a male subject (stored within module 300) is within that same pre-defined range of cycle variability scores and (ii) the Intermediate CAD Assessment value is less than that same pre-defined threshold by a value of amount Y. If both conditions are met (for a negative CAD assessment for the male subject having a certain cycle variability signature), the CVMGD compensation module 240 is configured to determine the final continuous CAD assessment score as the threshold value plus the amount Y (i.e., to provide a positive CAD assessment) in which Y is determined as a threshold value plus the difference the threshold value and the Intermediate CAD Assessment score. That is, the CVMGD modules adjusts the Intermediate CAD Assessment value to a magnitude value equivalent to, or same as, the threshold value plus Y. If the subject does not meet either of the above scenarios, then the subject's score is not modified by module 240 and the original value is passed through without change. If modified, this change embeds the information that, as previously specified, within a given range of cycle variability, a positive CAD assessment on men (as output from the combine predictions component 235) is more likely to be negative, and conversely, a negative CAD assessment on men is more likely to be positive.

In an example for module 240 with respect to the embodiment of FIG. 2, consider a male subject with (i) an Intermediate CAD Assessment score of 0.14460082598168 and a cycle variability score (maximum of ORTH1 and ORTH3) that is within the pre-defined (cycle variability) thresholds of 0.0071 and 0.0079 (greater than 0.0071 but less than 0.0079) and (ii) a pre-defined (CAD assessment) threshold of 0.13460082598168: in this case, the CAD assessment will be modified by the compensation operation performed by module 240 such that the subject is assigned an Intermediate CAD Assessment score of 0.124600825981680 (e.g., calculated as 0.13460082598168 minus a prior Intermediate CAD Assessment score of 0.14460082598168 minus the threshold value 0.13460082598168). Because the resultant final continuous CAD assessment score is now below the threshold of 0.13460082598168 by a difference that is between the threshold value and the input Intermediate CAD Assessment value), the Intermediate CAD Assessment score (which is was previously higher than the threshold value) is now adjusted to be lower than the threshold value. The modified score is then output from module 240. Indeed, a positive CAD assessment as generated by the Combine Predictions component 235 for male subjects is now outputted as a negative assessment.

The output of the assess signal quality module 300 and the CVGMD compensation component 240 are variously used in the subsequent termination processing performed by various termination blocks or modules/components, which in the system 200 of FIG. 2 include a final CAD prediction module 250, a generate localization predictions module 255, and a generate phase space volumetric data set/image module 260 (shown as "generate PST" 260).

Final CAD Prediction module 250 uses the final continuous CAD assessment from the CVMGD Compensation component 240 and provides the final binary CAD assessment as the output. In an implementation, if the final continuous CAD assessment is greater than or equal to the threshold of 0.13460082598168, then the subject is predicted CAD positive; otherwise, the subject is predicted CAD negative. The precision of the threshold value (e.g., 0.13460082598168) has 14 significant digits because the threshold value, as generated in this example, corresponds to a score belonging to a particular subject and can be used to identify the source of a threshold value during analysis and development. Values of such thresholds having various other degrees of precision may be used in other embodiments.

Generate Localization Predictions module 255 uses as input the final binary CAD assessment output from the Final CAD Prediction module 250 and the binary localization assessment of the subject's coronary arteries (e.g., LCX. LAD, RCA) and outputs a CAD localization assessment.

Generate PST module 260, in some embodiments, uses the unmodified PSR signal 205 (via the assess signal quality system 300) and outputs a PST data set/image. In other embodiments, the generate PST module 260 uses the PSR signal as pre-processed by other modules in the assessment system 110.

Figure 3:
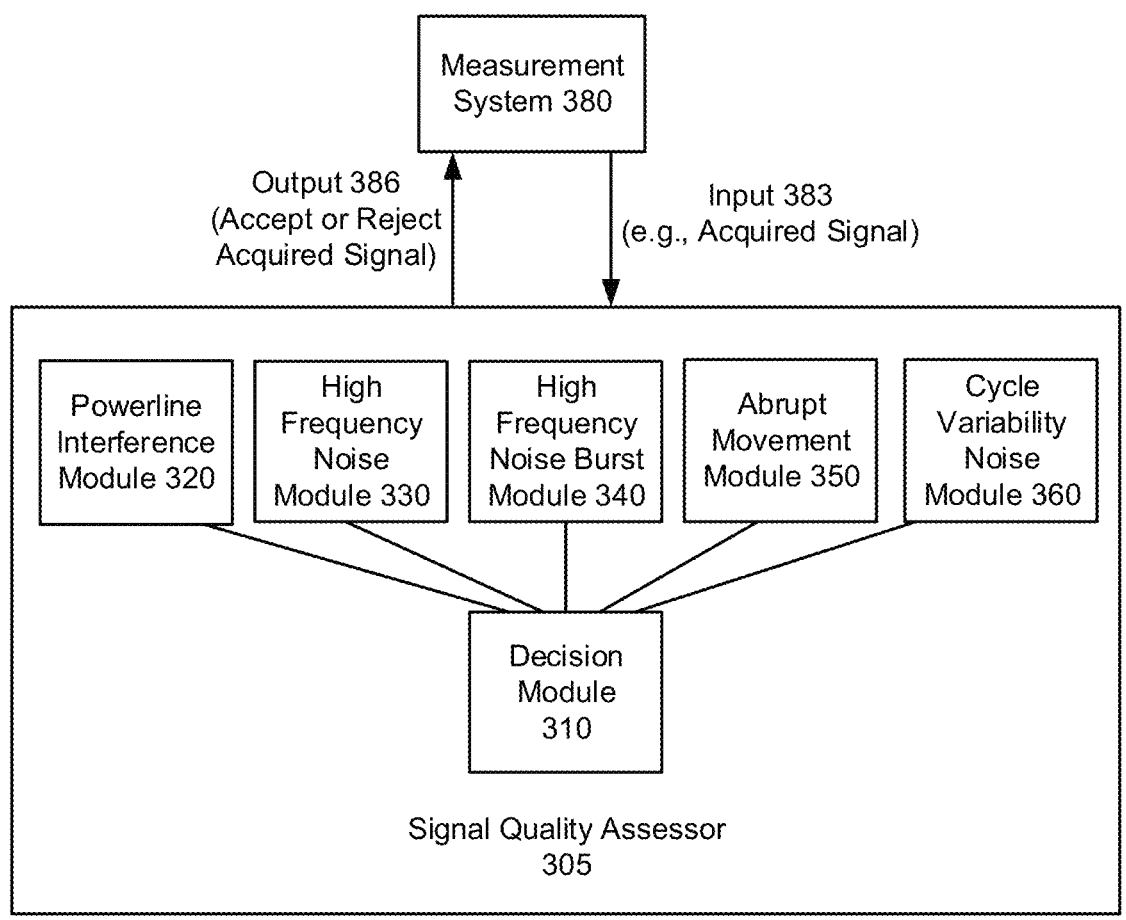
FIG. 3 is a diagram of an example signal quality assessment system in accordance with an illustrative embodiment.
Figure 4:
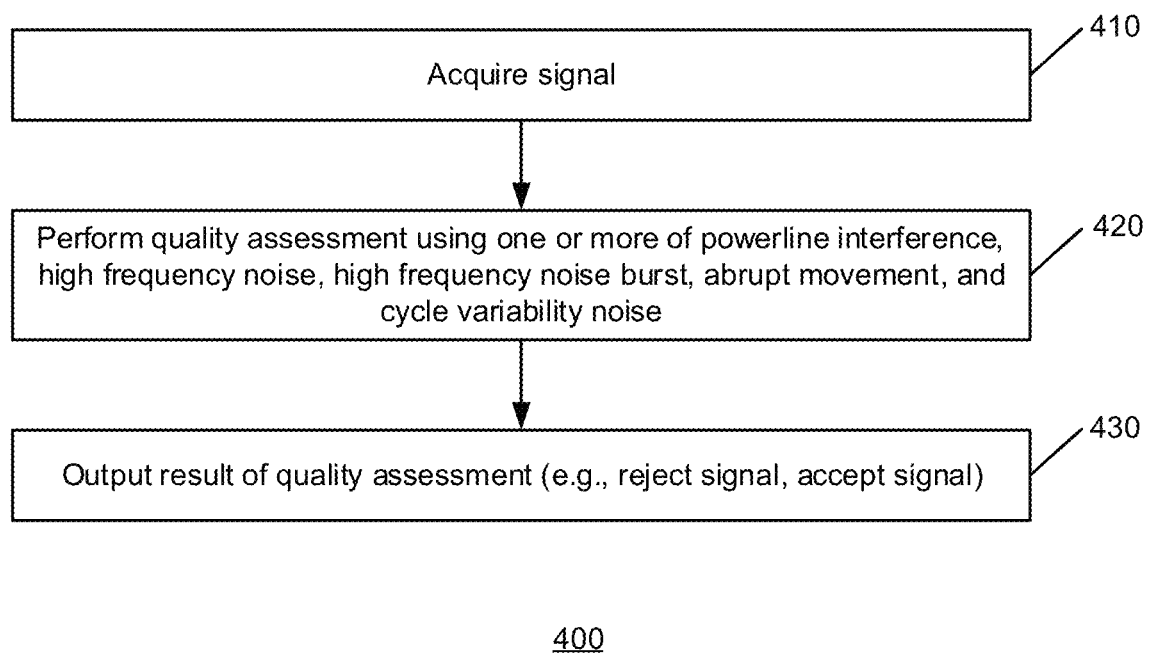
FIG. 4 is an operational flow diagram of an implementation of a method of assessing signal quality in accordance with another illustrative embodiment.

FIG. 3 is a diagram of an example signal quality assessment system 300, in accordance with an illustrative embodiment, and FIG. 4 is an operational flow diagram of an implementation of a method 400 of assessing signal quality, in accordance with another illustrative embodiment. The components the signal quality assessment system 300 combine to create an effective methodology for assessing signal quality that allows for subsequent analysis, his signal quality assessment method 400 can act as a gating stage for the subsequent analysis.

Figure 22:
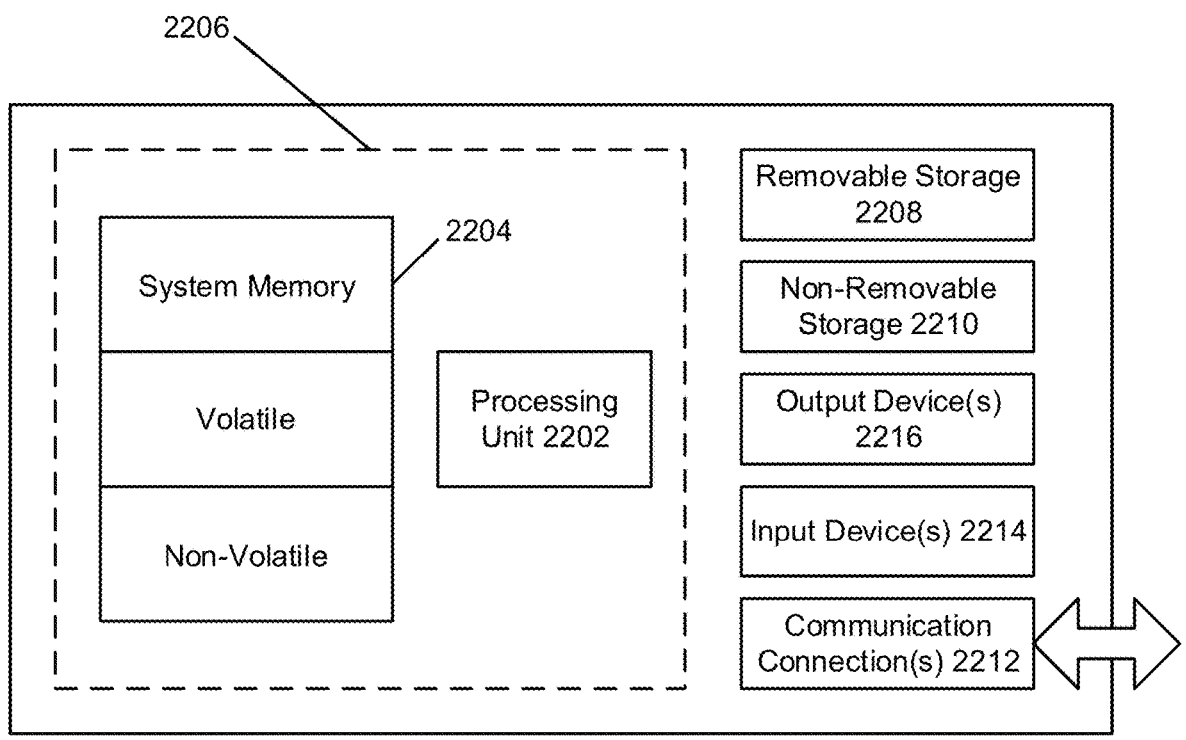
FIG. 22 shows an exemplary computing environment in which example embodiments and aspects may be implemented, in accordance with an illustrative embodiment.

The system 300 comprises a Signal Quality Assessor 305 and a Measurement System 380. The Signal Quality Assessor 305 and the Measurement System 380 may be comprised within the same computing device or may be comprised, as with all the components of the systems described throughout this disclosure, in separate computing devices that are in communication with each other (such as directly connected or coupled to each other, or communicatively connected or coupled to each other via a wired, optical, or wireless network). The network may be or comprised of one or more of a variety of network types including the public switched telephone network (PSTN), a cellular/mobile telephone network, a local area network such as a wired or wireless ethernet network (LAN), a network that includes near field communication (NFC) or other radio-frequency-based technologies and standards (e.g., Bluetooth®, Bluetooth® Low Energy, etc.), a packet switched network (e.g., the internet), etc. Although only one measurement system 380 is shown in FIG. 3, there is no limit to the number of Measurement Systems 380 that may be supported. The Signal Quality Assessor 305 and the Measurement System 380, as with all the components of the systems described throughout this disclosure, may each be implemented using one or more processors in connection with any variety of computing devices such as smartphones, smart watches, desktop computers, server computers, mainframe computers, laptop computers, tablet computers, and set top boxes (including any combinations thereof). Other types of computing devices may be supported. A suitable computing device is illustrated in FIG. 22 as computing device 2200.

Measurement System 380 may be any measurement system, such as measurement system 102, and Signal Quality Assessor 305 may be implemented separately or within Measurement System 102.

The quality of any electrical signal, including that of a biophysical signal such as a PSR signal as described herein (e.g., a signal acquired at about 8 kHz) can be affected by noise, which can originate from a variety of sources. Such noise can affect the acquired signal quality in a variety of ways. For example, noise can negatively affect the performance of subsequent analyses, such as those described herein relative to a clinical indication or disease state of a subject or patient. The impact of negative performance of subsequent analyses can manifest in a variety of ways. When processing is performed remotely (e.g., in a cloud service), a real-time or near real-time rejection of the signal facilitate the reacquisition or re-measurement of the patient, reducing patient inconvenience and cost in the patient having to come back to, e.g., the physician's office, hospital, or other clinical setting in order to reacquire the signals. Further, if the subsequent analysis involves the generation of a data set/or image (e.g., phase space data set/images) for interpretation by a physician, then the image may not correctly represent the physiological state of the subject and therefore lead to a misinterpretation, potentially resulting in delayed or incorrect diagnosis and/or treatment. If the subsequent analysis involves the explicit quantitative assessment of a given disease state of a subject, then negative performance could involve an incorrect quantification of the disease state, which may result in delayed or incorrectly withheld treatment, or the unnecessary use of additional testing or interventions, which may introduce the possibility of harm to the patient. Furthermore, independent of the type of analysis, noise may extend the processing time and/or cost (in computational resources) to produce an output. Therefore, it may be useful to identify and quantify noise so that it may be, in whole or in part, (or even in some cases along with the signal(s) with which it is associated) excluded, minimized, or otherwise processed—thus eliminating or minimizing such negative effects. Examples of noise relevant to the present disclosure include, for example, powerline interference, high frequency noise, high frequency noise bursts, (abrupt) baseline movement, and cycle variability. For purposes of the present disclosure, any unwanted disturbance in the signals disclosed herein, regardless of its source, may be considered "noise".

As seen in the exemplary method illustrated in FIGS. 3 and 4, at Acquire Signal step 410, Measurement System 380 acquires an input signal 383, such as PSR signal 205, and provides it to the Signal Quality Assessor 305. The input signal 383 may be an acquired biophysical signal or biophysical-signal data set of a subject. For cardiac signals, a hand-held or other device may be used to collect a subject's resting thoracic physiologic signals, e.g., from a single probe/sensor or a set of any number of probes/sensors or electrodes (e.g., six probes 114a-114f), arranged in the case of, e.g., six probes, along three orthogonal axes corresponding to ORTH1, ORTH2 and ORTH3 channels as described above. The electrodes, as part of non-invasive measurement system 102, can acquire the phase-gradient biophysical signals (to which the biophysical signal data set 108 is derived described above) without the use of ionizing radiation, contrast agents, exercise, or pharmacologic stressors; however, in some embodiments, the biophysical signals of interest can nevertheless be used in combination with such protocol or equipment. The non-invasive measurement system 102, in some embodiments, samples at about 8 kHz for a duration of between about 30 and about 1400 seconds, preferably for about 210 seconds. The acquired data points are transferred as part of the biophysical signal data set 108 to the assessment system 110 and evaluated, for example, by an analytic engine therein employing machine-learned algorithms/predictors. Other electrode sets and electrographic acquisition methodologies may be used to which the methods and systems disclosed herein can be applied.

As described further herein, at step 420, signal quality assessor 305 uses one or more of a Powerline Interference module 320, a High Frequency Noise module 330, a high Frequency Noise Burst module 340, an Abrupt Movement module 350, and a Cycle Variability Noise module 360, any of which or all in conjunction with a Decision module 310, to perform a quality assessment and generate an output, such as output 386. The signal quality assessor 305, and/or one or more of the powerline interference module 320, the High Frequency Noise module 330, the High Frequency Noise Burst module 340, the Abrupt Movement module 350, the Cycle Variability Noise module 360, and/or the Decision module 310, may reside or otherwise be disposed on or within the device or apparatus that houses or otherwise comprises the measurement system 102 or the assess signal quality system 300, or be located locally, remotely (e.g., servers/processors, software and services residing and/or operating in the "cloud" and in communication with local servers/processors via a network such as the internet, etc.), or a hybrid system/arrangement in which some of the quality assessment evaluation is performed on-device and some of the quality assessment evaluation is performed remotely. An example of a suitable device or apparatus is illustrated in FIG. 22 as computing device 2200.

At step 430, output 386 is provided to measurement system 380 and the user. In an implementation, output 386 comprises an indicator to accept or reject the acquired signal(s) for subsequent processing and analysis (e.g., to be performed by the intermediate processing components and termination processing components described with respect to FIG. 2).

In an implementation, the input signal 383 is an unmodified PSR signal (channel data from ORTH1, ORTH2, and ORTH3 as parsed out of the PSR file downloaded from the PSDR (phase signal data repository)). As noted above, data from channel "ORTH1" corresponds to a bipolar acquisition channel data series that is recorded by the phase space recorder from electrodes 114 that are placed along or near one an orthogonal axis of a subject that passes through the subject's body from a left side to a right side of the subject. Data from channel "ORTH2" corresponds to a second bipolar acquisition channel data series that is recorded by the phase space recorder from two other electrodes 114 that are placed along or near the second of an orthogonal axis that passes through the subject's body in the superior side to the inferior side of the subject. And data from channel "ORTH3" corresponds to a third bipolar acquisition channel data series that is recorded by the phase space recorder from two further electrodes 114 that are placed along or near the third an orthogonal axis that passes through the subject's body in the anterior direction to the posterior direction. Signals of ORTH1, ORTH2, and ORTH3, and their corresponding data sets, can be arranged, e.g., in phase space coordinates, in mutually orthogonal axes.

In an implementation, output 386 comprises an assessment of whether or not to proceed with further analysis, and the time window of the signal that is suitable for analysis, which ultimately is used to determine if a patient is considered CAD positive.

As described further with respect to FIGS. 3 and 5-7, Powerline Interference module 320 detects or otherwise determines powerline interference noise (e.g., noise introduced by a 60 Hz powerline (the frequency commonly used in regions such as Canada, South Korea, Taiwan, United States, and some regions of Japan) and its harmonics; noise introduced by a 50 Hz powerline (the frequency commonly used in regions such as China, France, Germany. Hong Kong, India, Italy, Switzerland, U.K., and some regions of Japan) and its harmonics). The determined powerline interference noise is provided to Decision module 310 for processing; e.g., as described further herein.

As described further with respect to FIGS. 3 and 8-10, High Frequency Noise module 330 detects or otherwise determines excessive signal frequency content (e.g., greater than 170 Hz in an implementation, where the frequency content above 170 Hz is not necessarily periodic, and can include pulses and other such artifacts). The output of High Frequency Noise module 330 is provided to decision module 310 for processing; e.g., as described further herein.

As described further with respect to FIGS. 3 and 11-13, the High Frequency Noise Burst module 340 detects or otherwise determines short bursts of the above excessive high frequency content. The output of High Frequency Noise Burst module 340 is provided to decision module 310 for processing, e.g., as described further herein.

As described further with respect to FIGS. 3 and 14-16, Abrupt Movement module 350 detects or otherwise determines extreme baseline wander localized in specific segments of the signal, in which the wander is significant enough to cause distortion of the signal. The output of Abrupt Movement module 350 is provided to Decision module 310 for processing; e.g., as described further herein.

As described further with respect to FIGS. 3 and 17-19, Cycle Variability Noise module 360 provides quantification of noise that is asynchronous to the cardiac cycle, which can include voltage potentials generated by skeletal muscle activation. The output of Cycle Variability Noise module 360 is provided to decision module 310 for processing; e.g., as described further herein. The concepts described herein may be applied to quantifying noise that is asynchronous to other cyclic physiological signals outside the cardiac context.

In an implementation, the assessments described herein are performed at the channel-level; e.g., are evaluated independently on ORTH1, ORTH2, ORTH3 channels, and merged at a later stage of processing.

Figure 5:
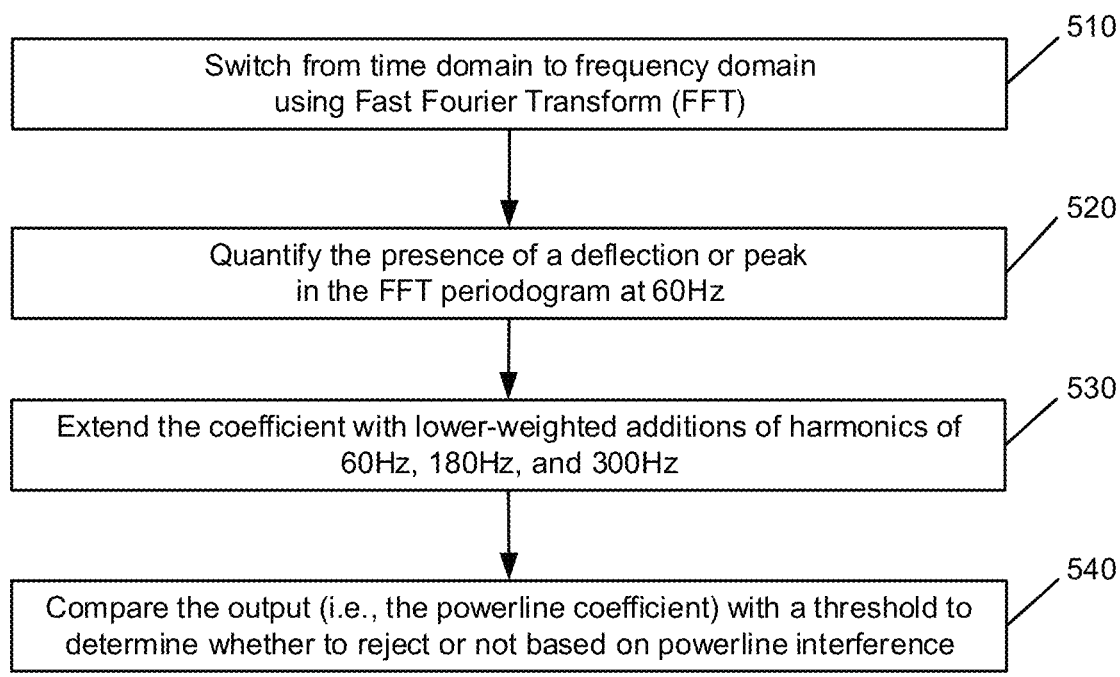
FIG. 5 is an operational flow diagram of an implementation of a method of assessing powerline interference, in accordance with another illustrative embodiment.

FIG. 5 is an operational flow diagram of an implementation of a method 500 of assessing powerline interference, in accordance with another illustrative embodiment. In an embodiment, a powerline coefficient can be an indicator of contamination of powerline noise, with higher values indicating higher contamination.

At step 510, the powerline coefficient is calculated by switching from the time domain to the frequency domain using a Fast Fourier transform (FFT). At step 520, the presence of a deflection or peak in the FFT periodogram is quantified at 60 Hz, for example. In some embodiments, the method include determining a base local frequency energy through the average decibel value between 55 Hz and 58 Hz and between 62 Hz and 65 Hz (e.g., base=abs(mean(power (55≤freq≤58 or 62≤freq≤65))) to provide a baseline power from which to detect if there is a peak occurring in the middle of that range (e.g., between 58 Hz-62 Hz). The method then determines a maximum powerline energy through the maximum decibel value between 58 Hz and 62 Hz (e.g., peakHeight=base-abs(mean(power(58≤freq≤62)) to quantify the peak between 58 Hz and 62 Hz. The method then determines a ratio of the height of the peak above the base as compared to the base (e.g., base+peakHeight/base). In essence, the determined ratio quantifies the presence of a deflection (or peak) in the FFT periodogram at 60 Hz.

At step 530, the powerline coefficient is further extended with inclusion of lower-weighted additions of harmonics (from 60 Hz) at 180 Hz and 300 Hz, which are calculated using the same methodology as described above with respect to the powerline coefficient for 60 Hz. It is contemplated that other frequencies and harmonics may be used depending on the implementation. The output from this assessment is the powerline coefficient for each of the ORTH1, ORTH2 and ORTH3 channels with the base name (only modified to indicate the data channel) of "powerlineCoef". At step 540, the output (i.e., the powerline coefficient) is determined as a score that is compared to a threshold value to determine whether or not to reject the input signal based on powerline interference. In some embodiments, the powerline coefficient score is determined as $10^{(powerline\ coeff_{60Hz}+0.5*powerline\ coeff_{180Hz}+0.25*powerline\ coeff_{300Hz})}$.

(Equation 8). In an implementation, if the powerline coefficient is greater than a threshold value of 486.6, then the signal is rejected based on powerline interference. In some implementations, there may be a geographic consideration when quantifying this score; e.g., with respect to the device being used. For example, for regions using 50 Hz, the calculation of the score may be modified to quantify 50 Hz powerline noise.

Note that graphs are used herein (e.g., FIGS. 6, 7, 9, 10, 12, 13, 15, 16, 18, 19) to assist in the description of the different types of noise and share common types of labels; time is along the bottom axis (in time-points in the unit of samples), where it is reflected as number of data points in an 8 kHz signal (8000 samples per second are being acquired), and amplitude is along the vertical axis. Amplitude in these figures is shown in mV; however, in some implementations, a normalized amplitude may be used that entails removing the average of the signal and dividing by the standard deviation (and thus, converting the signal to the z-score; e.g., the number of standard deviations from the mean a data point is, with the sign indicating the directionality).

Figure 6:
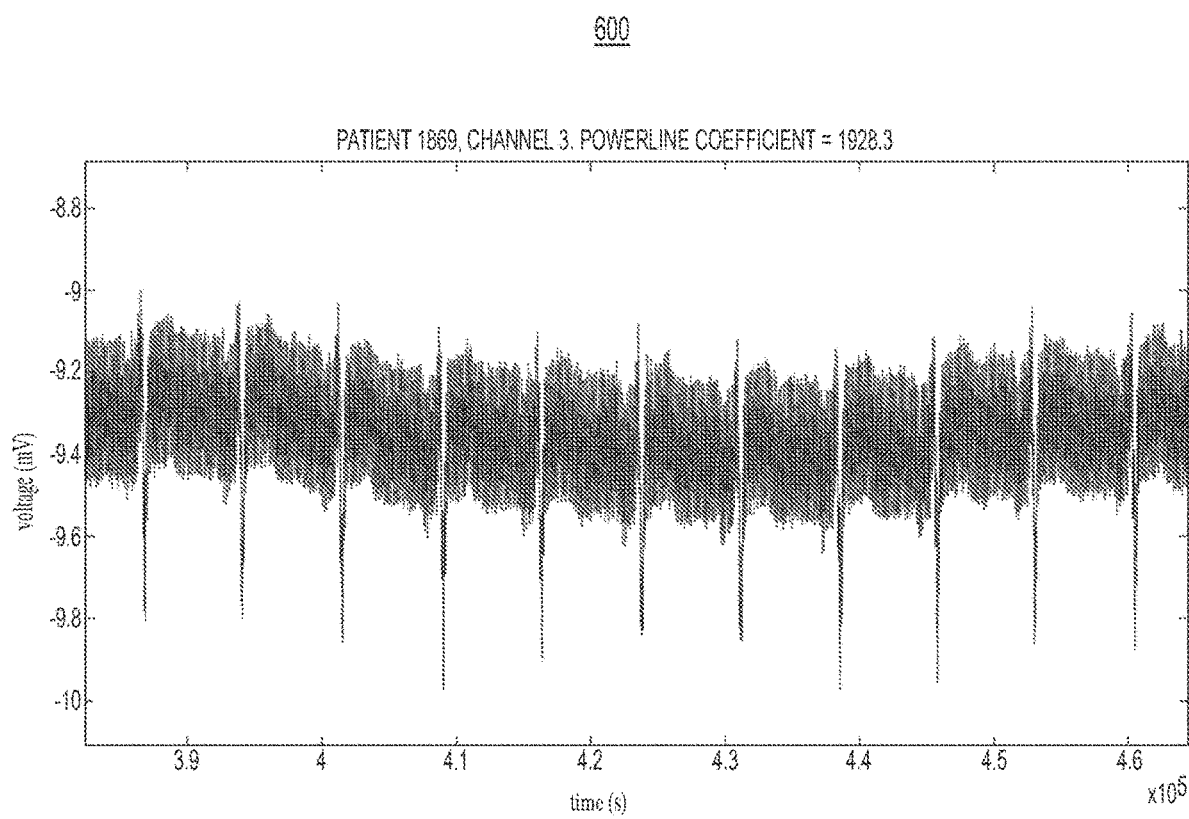
FIG. 6 is a graph illustrating observable characteristics of maximum powerline interference, e.g., of the powerline interference assessment operation of FIG. 5, in accordance with another illustrative embodiment.

For example, FIG. 6 is a diagram 600 illustrating observable characteristics, e.g., of maximum powerline interference in the cardiac context of the powerline interference assessment operation of FIG. 5, in accordance with another illustrative embodiment. FIG. 6 shows the maximum powerline coefficient on the channel-level. The powerline interference is clearly visible between the ventricular depolarization signals as periodic oscillations in the amplitude range of −9.15 mV to −9.45 mV.

Figure 7:
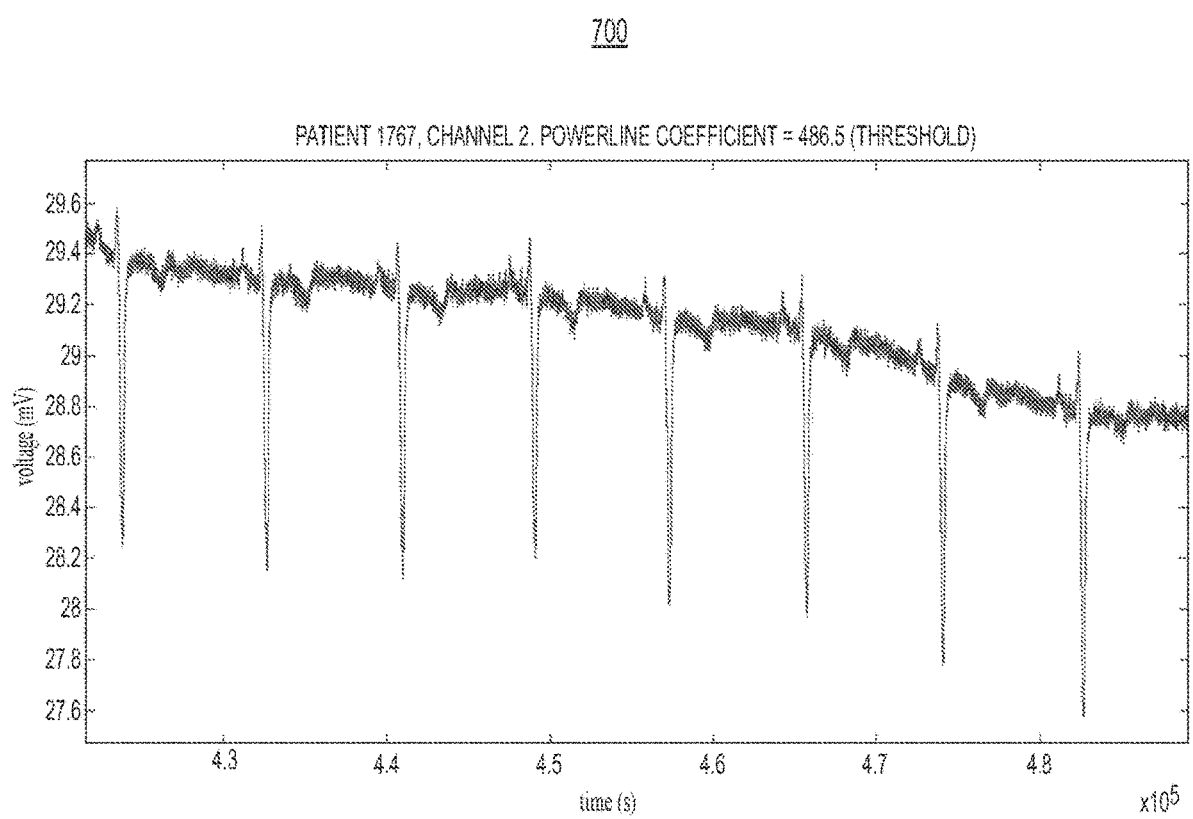
FIG. 7 is a graph illustrating observable characteristics of powerline interference at threshold, e.g., of the powerline interference assessment operation of FIG. 5, in accordance with an illustrative embodiment.

FIG. 7 is a diagram 700 illustrating observable characteristics of powerline interference at threshold, e.g., of the method of powerline interference assessment operation of FIG. 5, in accordance with an illustrative embodiment. FIG. 7 shows a powerline coefficient that is narrowly acceptable; e.g., the first coefficient that would be accepted, with anything higher being rejected. That is, the powerline coefficient for 60 Hz was found to be accepted in this data, but the powerline coefficient for 180 Hz and 300 Hz was found not to be acceptable.

Figure 8:
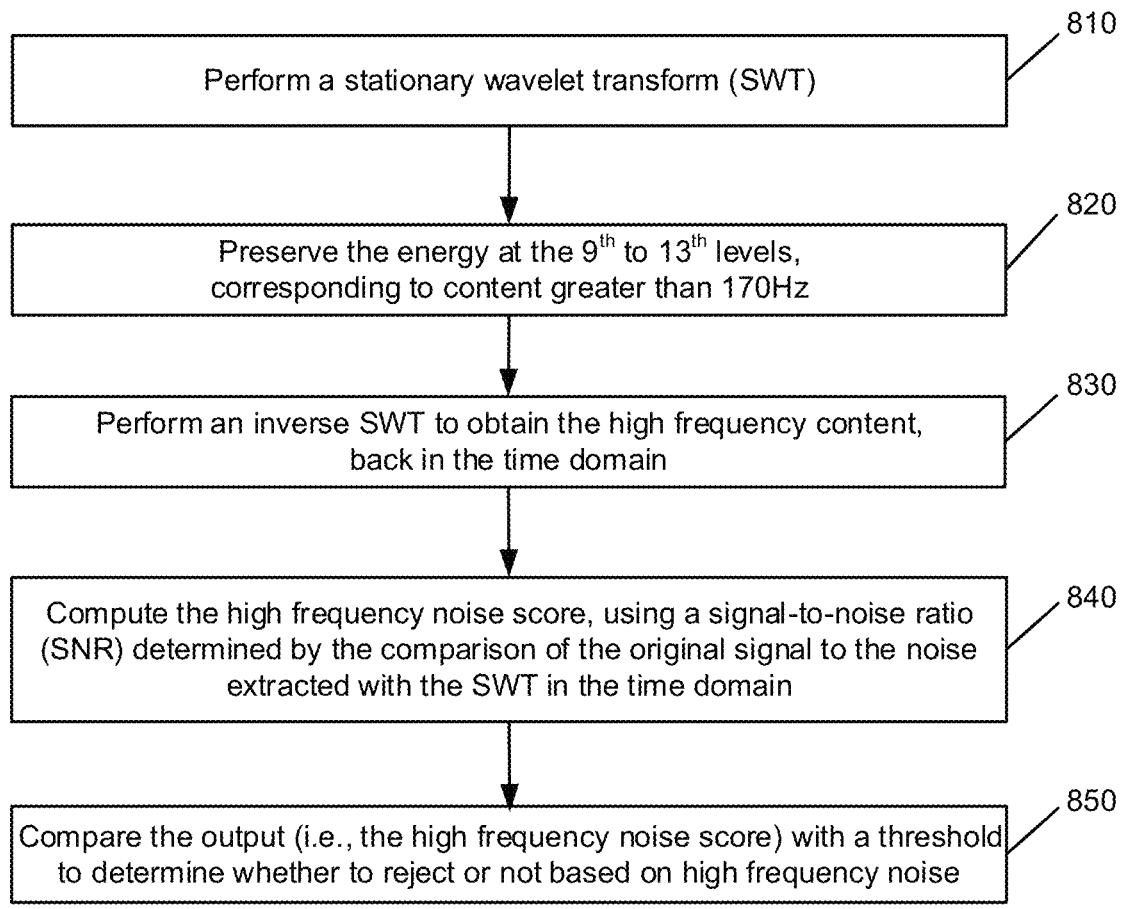
FIG. 8 is an operational flow diagram of an implementation of a method of assessing high frequency noise, in accordance with an illustrative embodiment.

FIG. 8 is an operational flow diagram of an implementation of an exemplary method 800 of assessing high frequency noise, in accordance with an illustrative embodiment. The high frequency noise score is computed by first performing a stationary wavelet transform (SWT) at 810. Note that this is functionally similar to a Fast Fourier transform, except that SWT allows for frequency localization in time at the expense of frequency detail. At step 820, the energy at the 9th to 13th levels is preserved, corresponding to content greater than 170 Hz, and then at step 830 an inverse SWT is performed. The result of these transformations is the high frequency content, back in the time domain (where it is visible, if that intermediate output was plotted).

At step 840, the signal-to-noise ratio (SNR) is computed as the high frequency noise score through the comparison of the original signal to the noise extracted with the SWT in the time domain. The output from this evaluation has the base name "hfNoiseToSignalRatio", which is only modified to indicate the source channel.

At step 850, the output (i.e., the high frequency noise score) is compared with a threshold to determine whether or not to reject the input signal based on high frequency noise. In an implementation, if the high frequency noise score is greater than 0.05273, then the signal is rejected based on high frequency noise.

Figure 9:
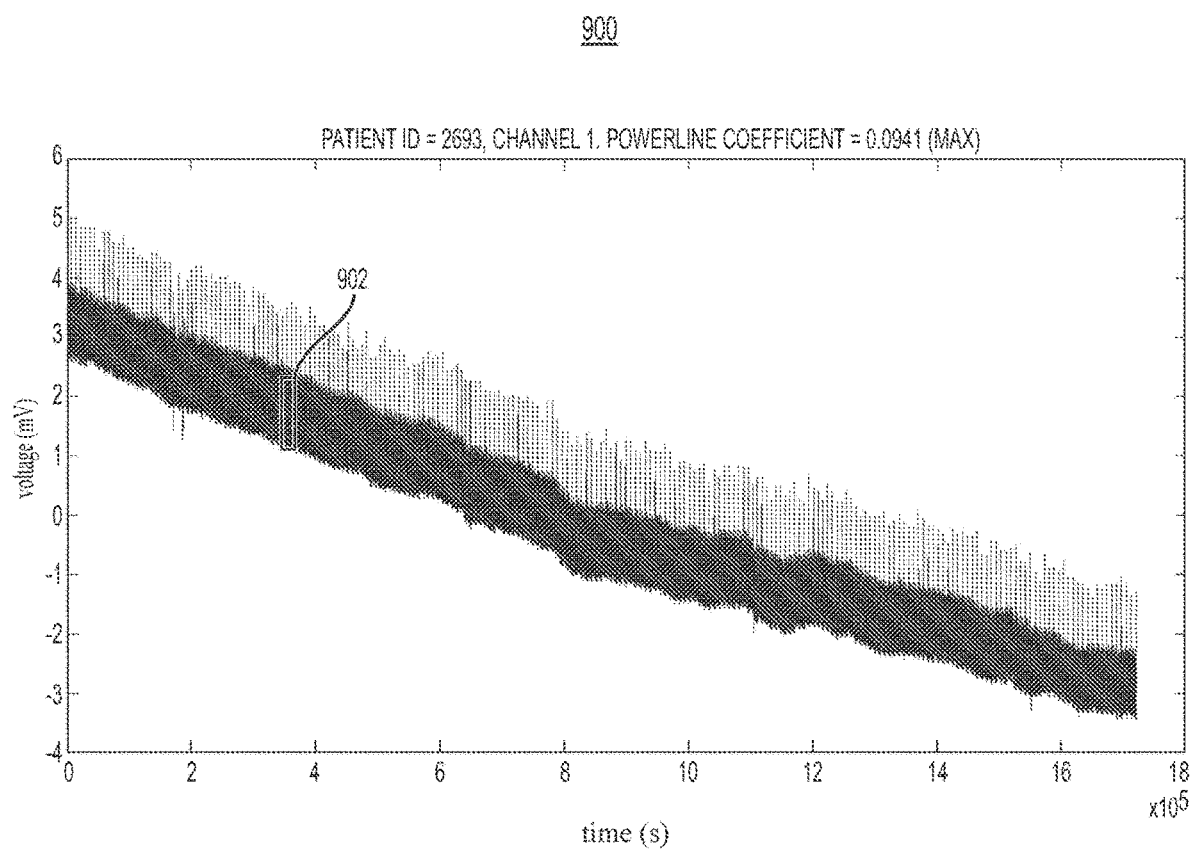
FIG. 9 is a graph illustrating observable characteristics of maximum high frequency noise, e.g., of the high frequency noise assessment operation of FIG. 8, in accordance with an illustrative embodiment.

FIG. 9 is a diagram 900 illustrating observable characteristics of maximum high frequency noise in the cardiac context, e.g., of the high frequency noise assessment operation of FIG. 8, in accordance with an illustrative embodiment. Here, the high frequency noise is visible as the thick dark line indicated for example in FIG. 9 as partially enclosed by box 902. This noise in FIG. 9 starts at the amplitude range from about 3 mV to about 4 mV, and trends down over time with a slow baseline wander to about −2 mV to about −4 mV.

Figure 10:
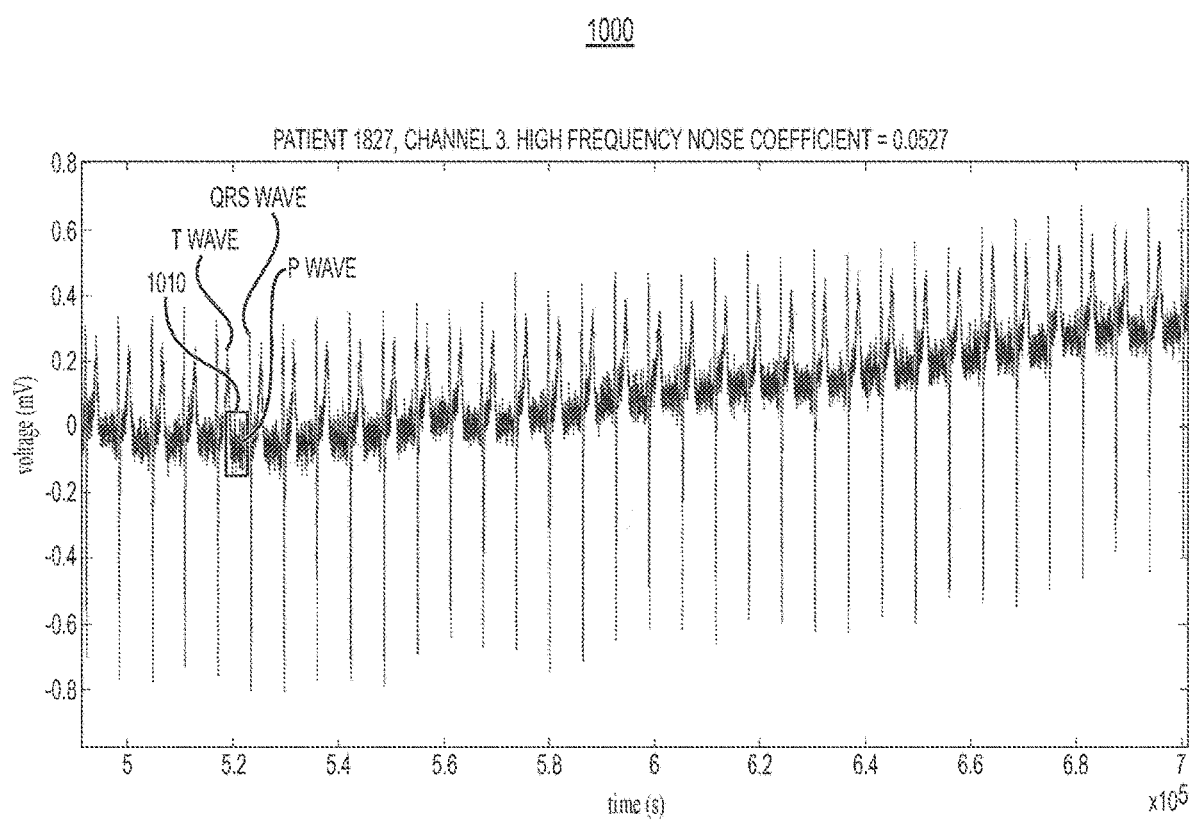
FIG. 10 is a graph illustrating observable characteristics of high frequency noise at threshold, e.g., of the high frequency noise assessment operation of FIG. 8, in accordance with an illustrative embodiment.

FIG. 10 is a diagram 1000 of high frequency noise at threshold of the high frequency noise assessment operation of FIG. 8, in accordance with an illustrative embodiment in the cardiac context. Here, the signal is just acceptable. The x-axis time scale is smaller than that of FIG. 9, with the phase waveforms clearly distinguishable (e.g., QRS waveform, T waveform, etc.). The high frequency noise is visible in this particular example as impulses between the offset of the ventricular repolarization and the atrial depolarization events. The noise is most prominent all along the baseline— after the ventricular repolarization (e.g., "T-wave"), but before the atrial depolarization ("P-wave"), as indicated for example by box 1010. Such noise occurs in every cycle.

Figure 11:
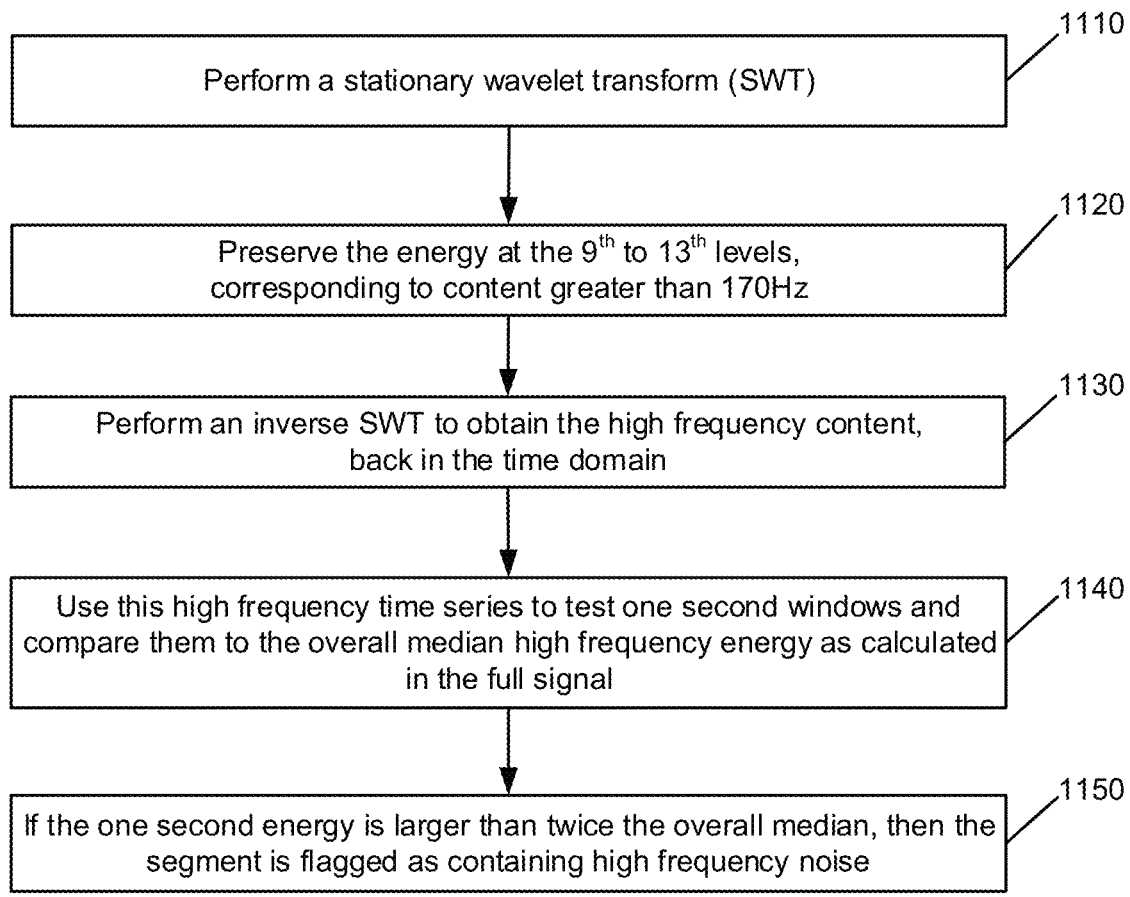
FIG. 11 is an operational flow diagram of an implementation of a method of assessing high frequency noise bursts, in accordance with an illustrative embodiment.

FIG. 11 is an operational flow diagram of an exemplary implementation of a method 1100 of assessing high frequency noise bursts. The score resulting from method 1100 quantifies the same high frequency noise as described with respect to FIG. 8 but is instead localized to one second segments. The value of this score, along with the abrupt or extreme baseline wander (described further herein), cannot in and of itself exclude a signal from subsequent analysis; however, that will occur if there is an insufficient signal length (e.g., a minimum of 16 consecutive seconds, and the same period across all channels) without high frequency noise bursts or abrupt baseline movement.

The computation of this score in connection with this exemplary method 1100 is similar to that of the overall high frequency score described elsewhere herein. For example, the high frequency component is extracted from the signal at steps 1110, 1120, and 1130 using the same or similar methods as described with respect to FIG. 8 (analogous steps 810, 820, and 830, respectively).

At step 1140, the illustrated exemplary process uses this high frequency time series data obtained in connection with step 1130 to test one second windows and compare the results to the overall median high frequency energy as calculated in the full signal. At step 1150, in an implementation, if the energy obtained in a given one second window or set of one second windows is larger than twice the overall median, then the segment is flagged as containing high frequency noise. In an implementation, any single one-second window can be flagged. For a set of one-second windows to be flagged, all must meet the same criteria as a one-second window, which is twice the overall median energy. Therefore, the standard is the same for a set of windows as it is for a single window.

In an implementation, the output from this evaluation are two scores modified to indicate the source data channel. For example, the scores may be output labeled as "medianHfSignalEnergy" (indicating overall median high frequency energy) and "hfNBCoefficient" (indicating the 1-second energy of any window that is larger than four times the medianHfSignalEnergy). If there are multiple such windows, then the maximum value is returned.

Figure 12:
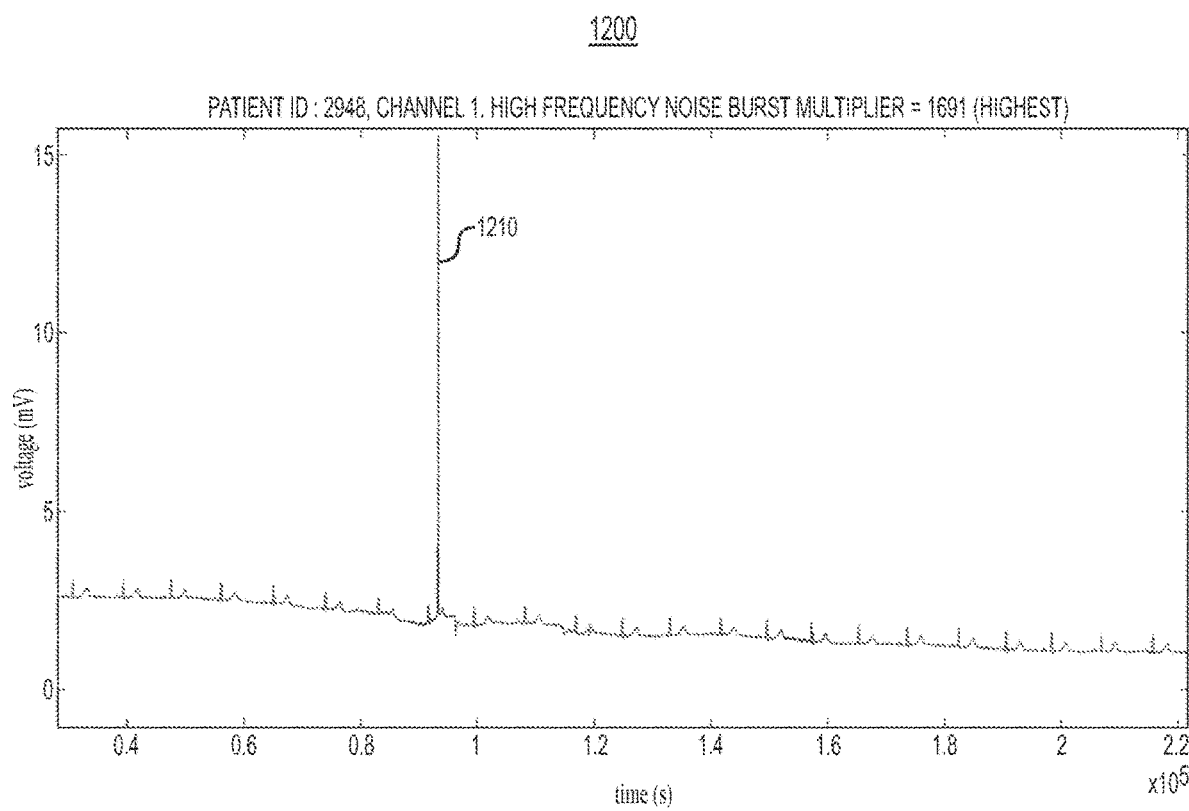
FIG. 12 is a graph illustrating observable characteristics of maximum high frequency noise burst, e.g., of the high frequency noise burst assessment operation of FIG. 11, in accordance with an illustrative embodiment.

FIG. 12 is a diagram 1200 illustrating observable characteristics of a maximum high frequency noise burst 1210, e.g., of the high frequency noise burst assessment operation of FIG. 11, in accordance with an illustrative embodiment. In this case, the high frequency noise burst 1210 is characterized as an impulse that lasts for a few data points (e.g., less than 1 millisecond). As in the other figures (FIGS. 6, 7, 9, 10, 13, 15, 16, 18, 19), the x-axis units are samples, and the y-axis units are mV (not normalized).

Figure 13:
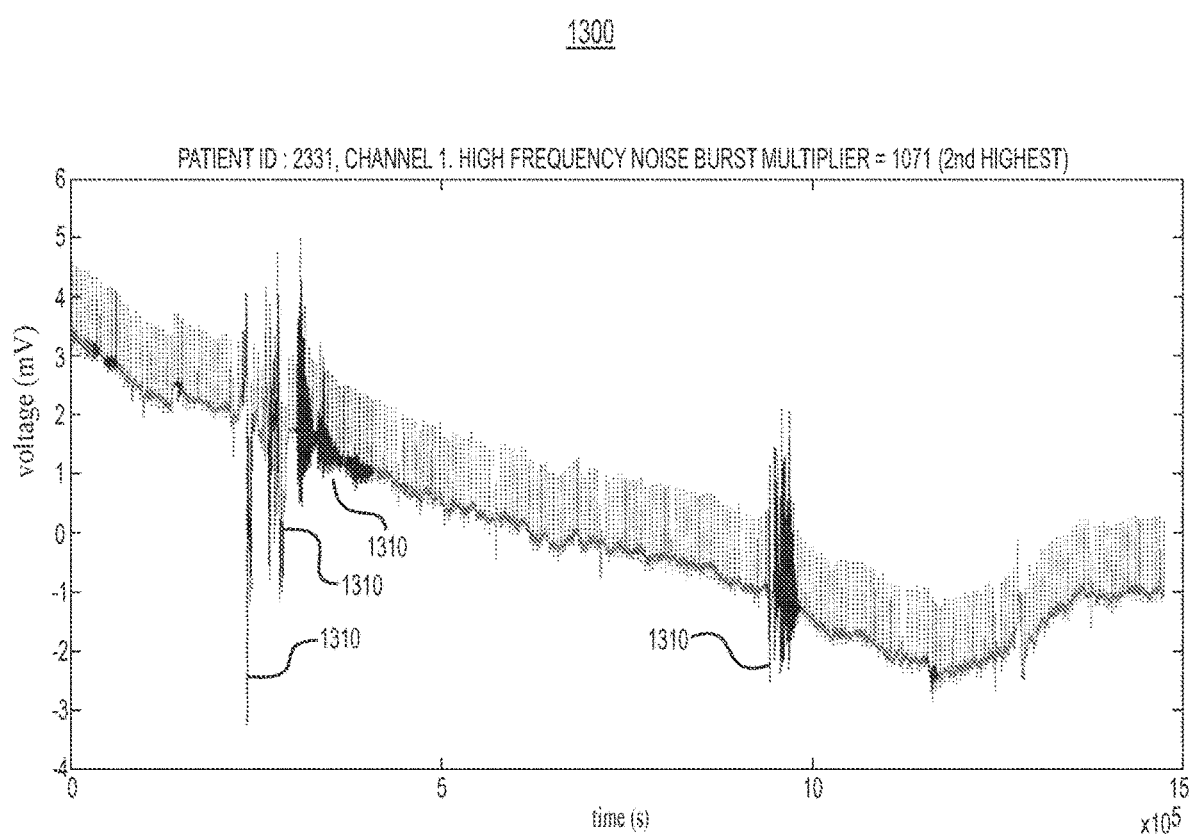
FIG. 13 is a graph illustrating observable characteristics of second highest high frequency noise burst, e.g., of the high frequency noise burst assessment operation of FIG. 11, in accordance with an illustrative embodiment.

FIG. 13 is a diagram illustrating another observable characteristics of high frequency noise burst diagram 1300, e.g., of the high frequency noise burst assessment operation of FIG. 11, in accordance with an illustrative embodiment. This is a more typical characteristics of high frequency noise burst than that depicted in FIG. 12, in which there are several high frequency bursts indicated at 1310 observed over the timeframe indicated.

Figure 14:
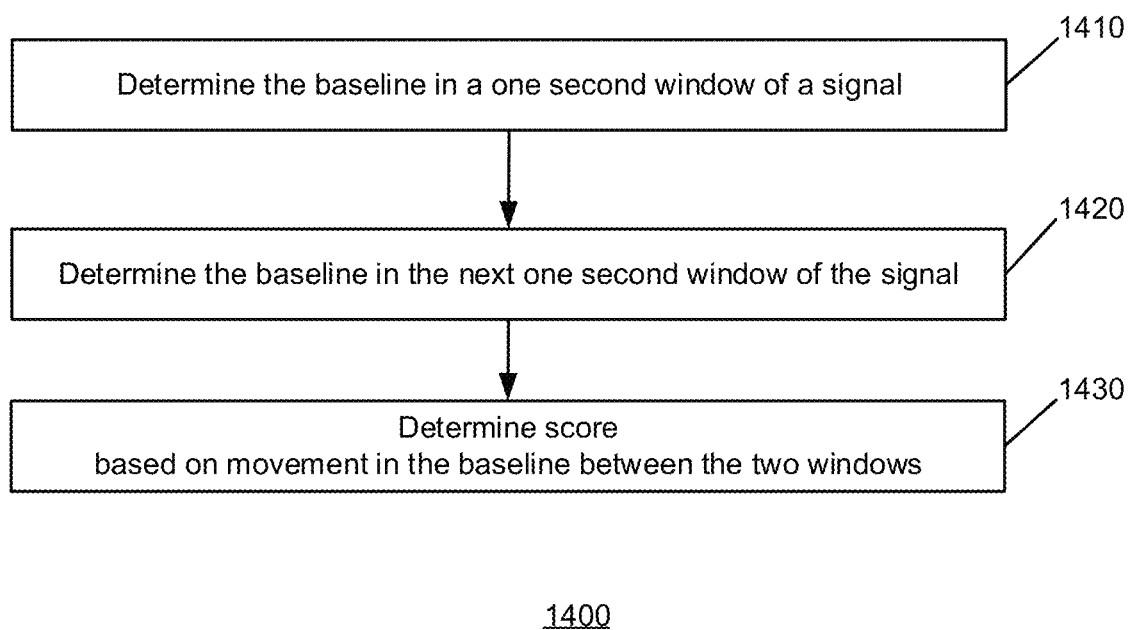
FIG. 14 is an operational flow diagram of an implementation of a method of assessing abrupt baseline movement, in accordance with an illustrative embodiment.

FIG. 14 is an operational flow diagram of an implementation of a method 1400 of assessing abrupt baseline movement, in accordance with an illustrative embodiment in the cardiac context. Movement in the baseline is defined, in this example, as "abrupt" if the baseline in a one-second window of a signal changes (relative to that in the previous window) by more than 25% of the ventricular depolarization amplitude of the channel. Other definitions of "abrupt" in this context may be established depending on the type of biophysical signal being acquired and analyzed, the physiological condition of the patient, and other factors as appropriate.

At step 1410, the baseline in a one second window of the input signal is determined. At step 1420, the baseline in the next one second window of the signal is determined. At step 1430, the score is determined based on movement in the baseline between the two windows.

In an implementation, if the movement within the window is less than 25%, then it is assigned a score of zero. If there are multiple movements greater than 25% in a one second window, then that window is assigned the maximum of those movements. The output from this evaluation has the base name of "maxAbruptMovementPercentage", which is only modified to reflect the source data channel.

Figure 15:
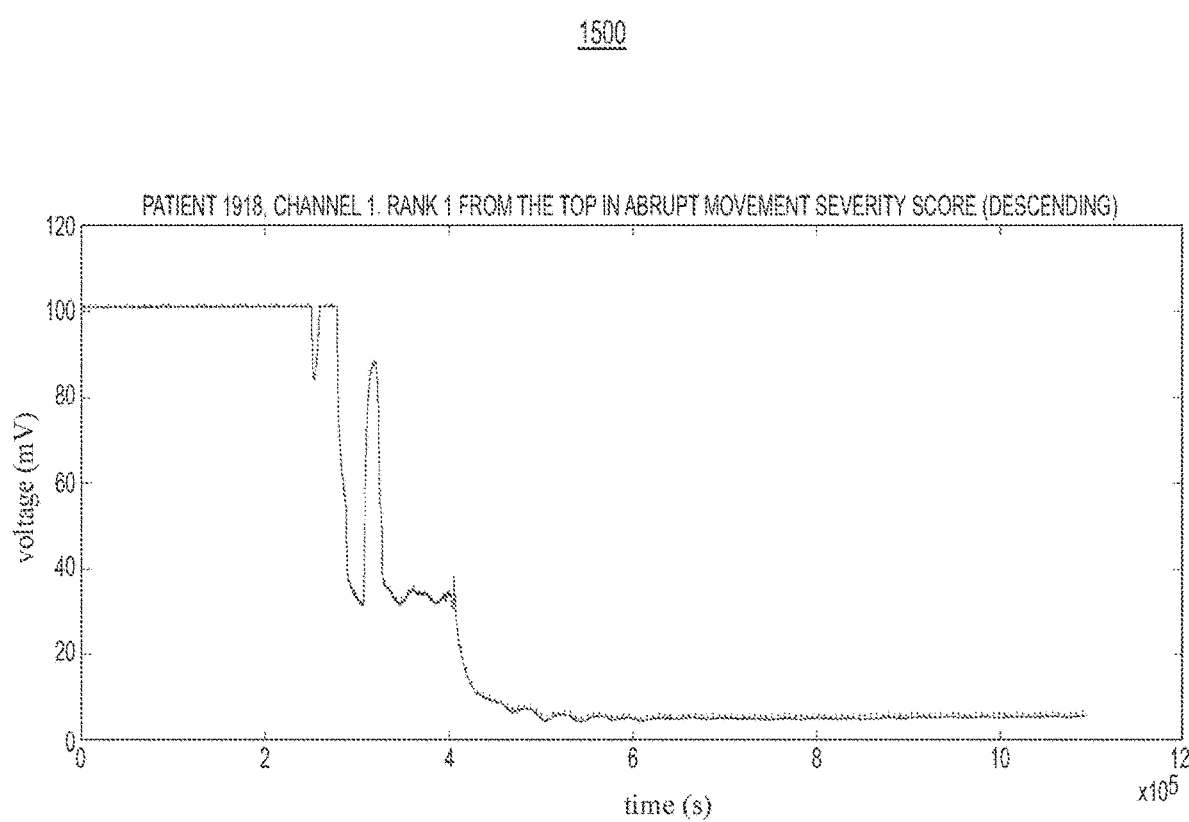
FIG. 15 is a graph illustrating observable characteristics of maximum abrupt movement, e.g., of the abrupt baseline movement assessment operation of FIG. 14, in accordance with an illustrative embodiment.

FIG. 15 is an exemplary diagram 1500 illustrating observable characteristics of maximum abrupt movement of a subject, e.g., of the abrupt baseline movement assessment operation of FIG. 14, in accordance with an illustrative embodiment in the cardiac context. Here, the phase signal is initially stable at an amplitude of 100 mV, but it is followed by first a dip in this baseline value around 20 mV followed by a massive dip down to around 30 mV. During those abrupt baseline changes, the phase signal is either severely diminished or not present.

Figure 16:
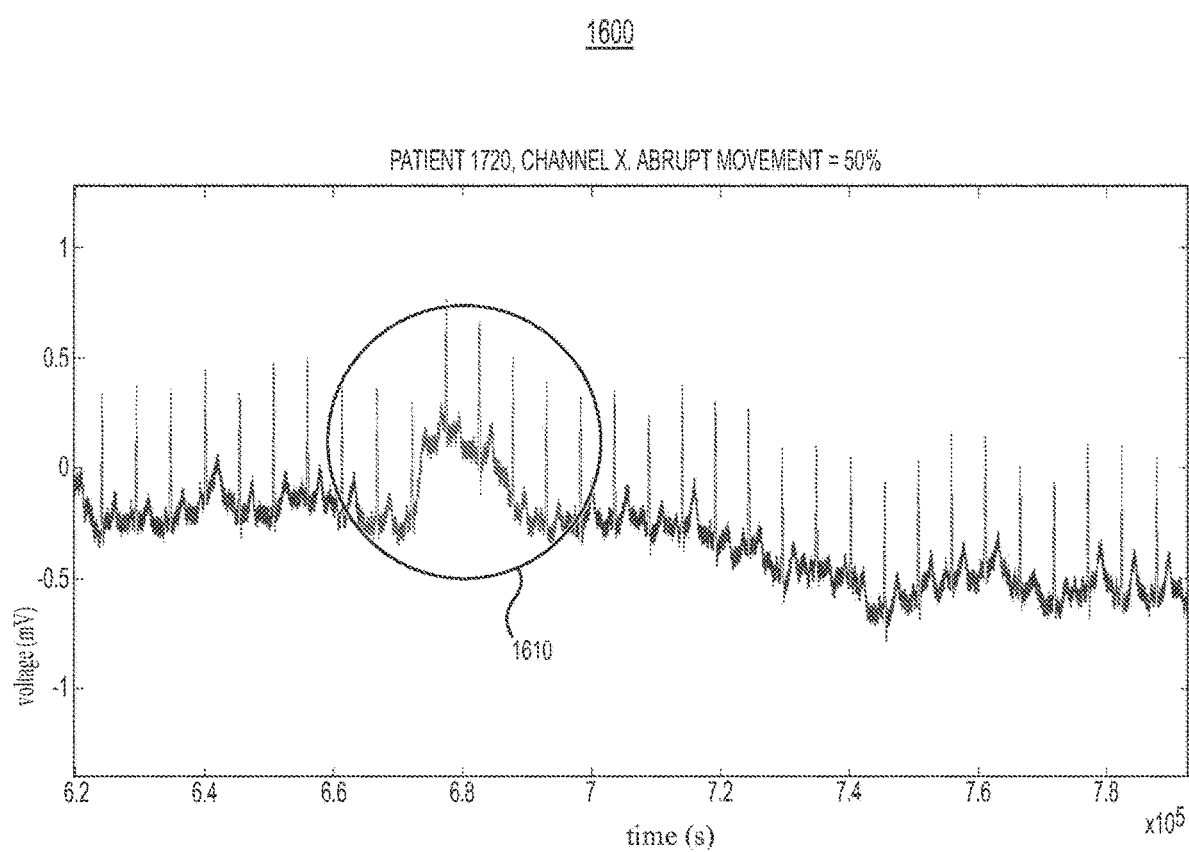
FIG. 16 is a graph illustrating observable characteristics of 50% abrupt movement, e.g., of the abrupt baseline movement assessment operation of FIG. 14, in accordance with an illustrative embodiment.

FIG. 16 is an exemplary diagram 1600 illustrating observable characteristics of abrupt movement of approximately 50%, e.g., of the abrupt baseline movement assessment operation of FIG. 14, in accordance with an illustrative embodiment in the cardiac context. This is a more typical example of abrupt baseline movement, shown here as 1610, which depicts an upward movement in the signal amplitude followed almost immediately by an equivalent downward movement, w % here that signal amplitude movement causes the ventricular depolarization event at the top of the movement to have an amplitude that is roughly 50% higher than the ventricular depolarization events prior to that 1-second window.

Figure 17:
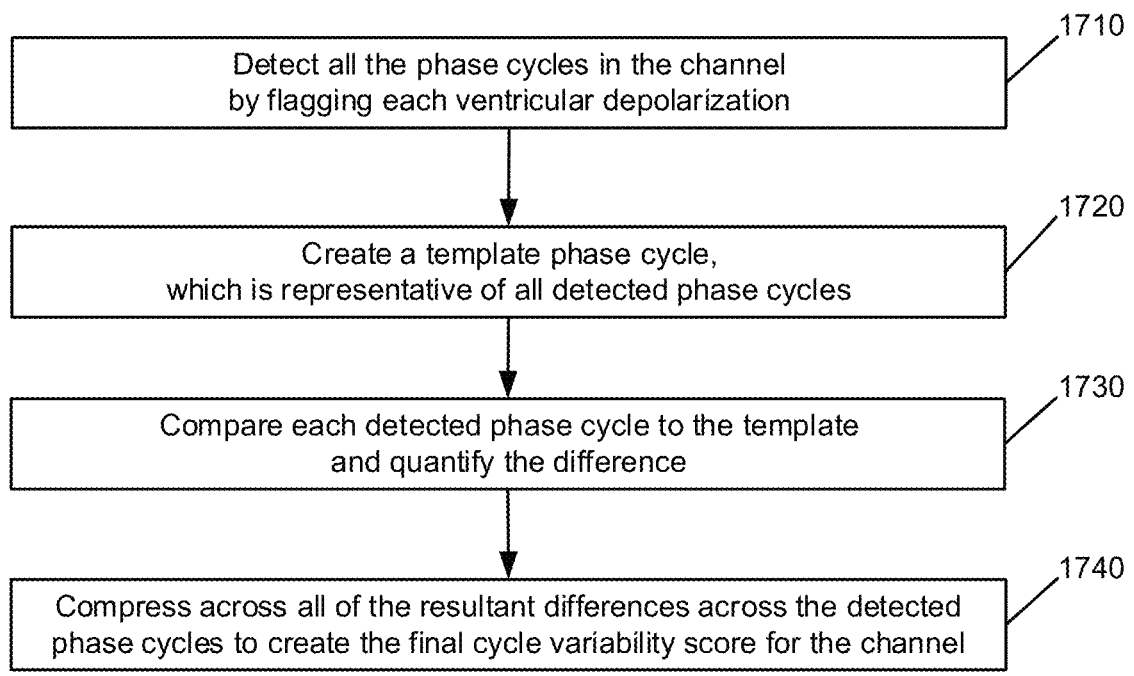
FIG. 17 is an operational flow diagram of an implementation of a method of assessing cycle variability, in accordance with an illustrative embodiment.

FIG. 17 is an operational flow diagram of an implementation of a method 1700 of assessing cycle variability, in accordance with an illustrative embodiment in the cardiac context. Examination of phase cycle variability (in cardiac systems as well as other physiological systems or combinations thereof) reveals asynchronous noise, which can quantify the presence of muscle noise artifacts as well as other types of noise that lack alignment with the phase cycle.

Cycle variability noise may be calculated using the exemplary technique of FIG. 17, which detects content that is in-band to the frequency range of the phase signal and that has a similar amplitude.

At step 1710, all the phase cycles in the selected channel are detected by flagging each ventricular depolarization event (e.g., the point in time during each phase cycle when the electrical activation of the ventricles is at a maximum).

At step 1720, a template phase cycle is created, which is representative of all detected phase cycles. At step 1730, each detected phase cycle is compared to the template and the difference is quantified.

At step 1740, the technique compresses across all of the resultant differences across the detected phase cycles to create the final cycle variability score for the channel.

In an implementation, the final cycle variability score is calculated for each of channels ORTH1 and ORTH3, and the greater of these two scores is used to generate the overall score for the signal. In this example, ORTH2 is excluded from this computation because it was found to have the highest final cycle variability score compared to that of ORTH1 and ORTH3—more than two-thirds of the time—much higher than one-third of the time (what would statistically be expected if the final cycle variability of each of the three channels had an equal likelihood of being the highest). Therefore, the inclusion of the final cycle variability score of the signals obtained from the ORTH2 channel would disproportionately influence or drive the value of the overall score compared to the contribution from the other two channels. However, in an alternate implementation, the maximum value may be calculated from all three channels (ORTH1, ORTH2, and ORTH3). This alternate maximum value would be expected to be higher than that based on ORTH1 and ORTH3; however, this technique enforces a more rigorous standard for signal quality which may be useful under certain circumstances.

In a human subject in the cardiac context, the ORTH2 vector typically spans from just below the subject's left clavicle straight down to just below the end of the ribcage, possibly resulting in two issues with signal acquisition that may, without wishing to be bound by theory, account for its associated higher final cycle variability score, and thus higher related noise level, compared to the other channels. First, the termination of the ORTH2 vector just below the ribcage places it on the stomach, and subjects being evaluated for CAD may tend to have a higher body mass index (BMI) as compared to the general population (BMI is a risk factor for CAD). Higher BMI typically indicates the presence of excessive abdominal fat, which changes the impendence across the two electrodes being used for signal acquisition. Second, the ORTH2 vector is perpendicular to the striations of the left pectoral muscle, possibly increasing the ability of noise related to the pectoral muscle to infiltrate and/or otherwise affect the signal. Muscle noise comes from contraction; however, contraction does not necessarily imply movement. For example, isometric contraction is the static contraction of a muscle without any visible movement in the angle of the joint.

Figure 18:
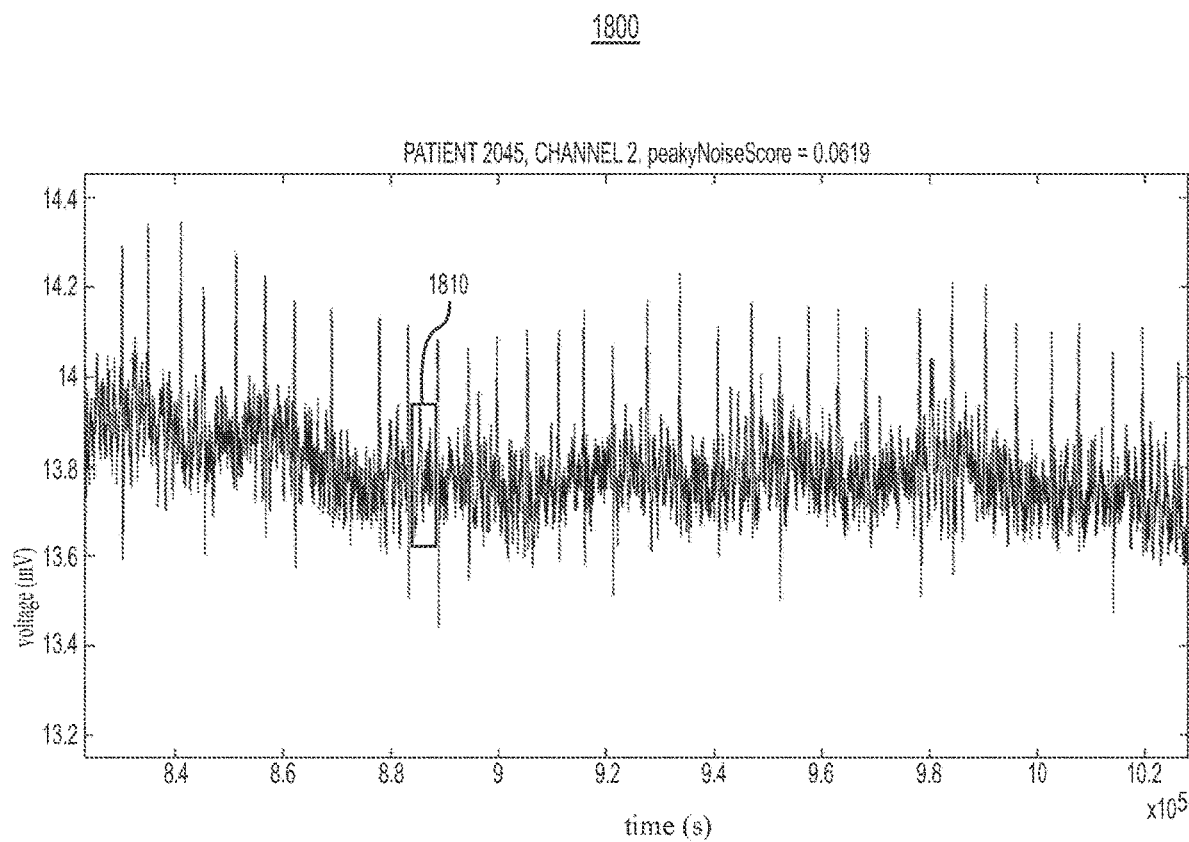
FIG. 18 is a graph illustrating observable characteristics of highest cycle variability noise, e.g., of the cycle variability assessment operation of FIG. 17, in accordance with an illustrative embodiment.

FIG. 18 is a diagram 1800 illustrating observable characteristics of highest cycle variability noise, e.g., of the cycle variability assessment operation of FIG. 17, in accordance with an illustrative embodiment in the cardiac context. The noise is most visible in between the phase cycles, in the period after the offset of the ventricular repolarization event and prior to the atrial depolarization event, appearing similar to extraneous phase waveforms (such as an additional ventricular repolarization event(s)). An example of this noise is indicated by box 1810. Note that the noise occurs on every cycle and is most visible in between the subject's heartbeats (e.g., QRS waveforms are shown as "spikes").

Figure 19:
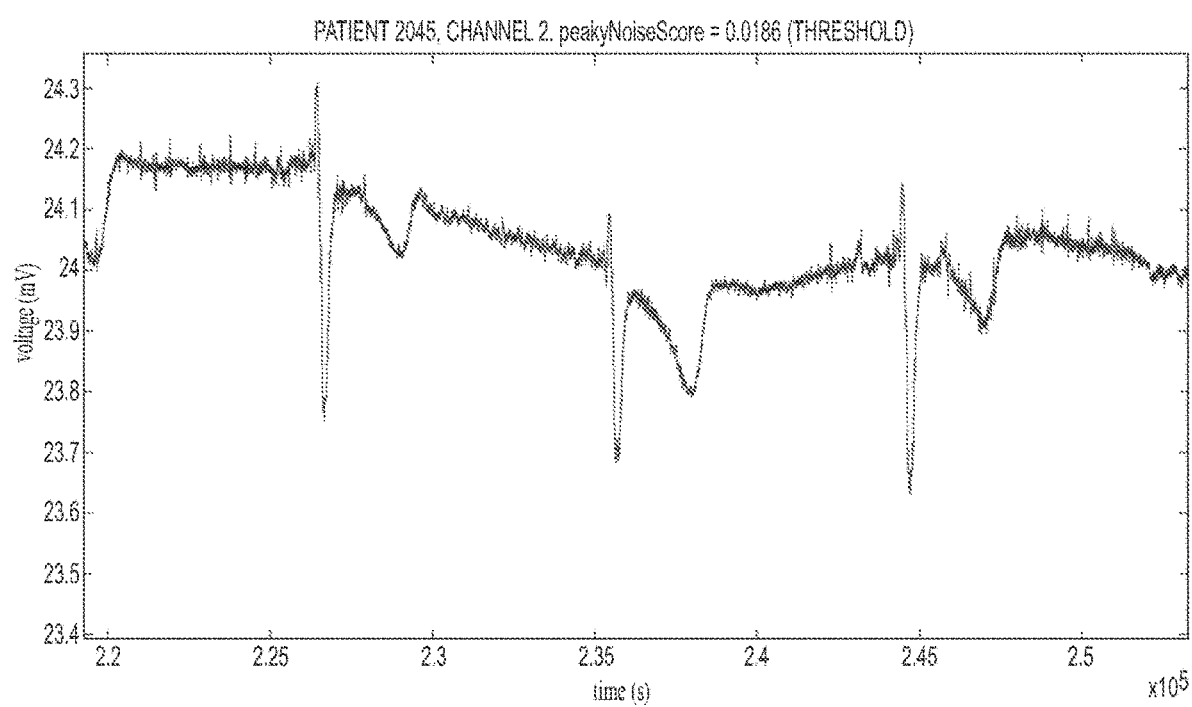
FIG. 19 is a graph illustrating observable characteristics of lower cycle variability noise, e.g., of the cycle variability assessment operation of FIG. 17, in accordance with an illustrative embodiment.

FIG. 19 is a diagram 1900 illustrating observable characteristics lower cycle variability noise, e.g., of the cycle variability assessment operation of FIG. 17, in accordance with an illustrative embodiment in the cardiac context. This diagram shows a lower level of noise contamination compared to the noise signature of, e.g., FIG. 18. Other differences are seen here as well, such as the noise having a relatively low frequency and a relatively high amplitude range, the latter resulting in a more impulse-like signature in the example of FIG. 19.

Figure 20:
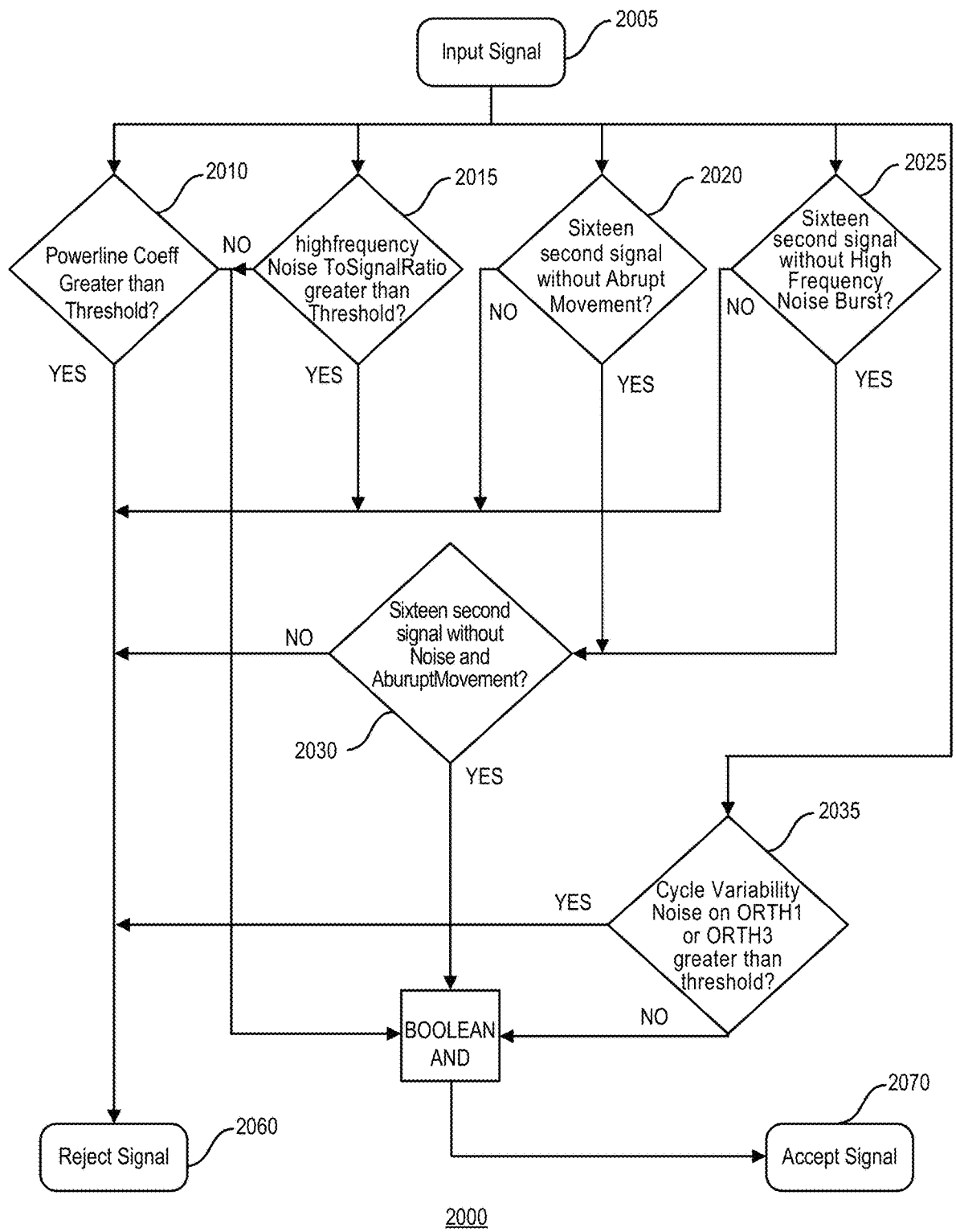
FIG. 20 is an operational flow diagram of an implementation of a method of assessing signal quality, in accordance with an illustrative embodiment.

FIG. 20 is an operational flow diagram of an implementation of a method 2000 of assessing signal quality, in accordance with an illustrative embodiment. In particular, the scores are assessed in the signal usability workflow described with respect to FIG. 20.

At step 2005, the input signal is received (e.g., PSR signal 205).

A powerline interference test is performed at step 2010 to determine if the powerline coefficient of the input signal is greater than a threshold. If so, then the input signal is rejected at step 2060. Otherwise, the input signal is considered to pass this test and in this example a binary number indicating a passed test #1 is provided to a Boolean "and" operator.

At step 2015, another high frequency noise test (test #2) is performed to determine if the high frequency noise-to-signal-ratio is greater than a threshold. If so, the input signal is rejected at step 2060. Otherwise, the input signal is considered to pass this test #2 and, in this example, a binary number indicating a passed test #2 is provided to a Boolean "and" operator.

At steps 2020, 2025 and 2030, abrupt movement tests (collectively, "test #3") are performed to determine if a clean signal segment is unavailable due to abrupt movement and high frequency noise bursts. If for any one or more of the component tests of test #3 at each of steps 2020, 2025 and 2030 indicates that such a clean signal segment is not available, the input signal is rejected at step 2060. Otherwise, the input signal is considered to pass each of the tests at steps 2020, 2025 and 2030 such that the input signal is test #3 and a binary number indicating a passed test is provided to a Boolean "and" operator.

At step 2030, a cycle variability test (test #4) is performed on the input signal to determine if there is cycle variability noise (e.g., on ORTH1 or ORTH3) that is greater than a threshold. If so, the input signal is rejected at step 2060. Otherwise, the input signal is considered to pass this test #4 and a binary number indicating a passed test #4 is provided to a Boolean "and" operator.

After the tests are completed and the aforementioned binary numbers have been provided to the Boolean "and" operator, this operator at step 2040 then performs a boolean operation based on these inputs, and if all the input binary numbers indicates passed tests, the input signal is accepted at step 2070. This logic provides that all tests must pass in order for the signal to pass and be accepted (step 2070). If any test fails, then the signal is rejected (step 2060).

Thus, for any given signal: (1) if any channel of the patient or subject fails the powerline interference metric test #1 at step 2010, the patient's input signal is rejected; (2) if any channel of the subject fails the high frequency noise metric, the subject's input signal is rejected; (3) if channel ORTH1, ORTH2, and/or ORTH3 of the patient fails the cycle variability threshold, the patient's input signal is rejected; (4) if abrupt movements or high frequency noise bursts are detected in the patient's input signal, an attempt is made to find at least one 16-second segment of the signal where abrupt movement or noise bursts are not detected, where that segment is the same across all channels (e.g., all channels are clean during that segment), and if such a window is not found, the patient's input signal is rejected, and otherwise (i.e., if such a window is found), the patient's input signal is processed using the found window; and (5) if all the channels of the patient's input signal pass all the metrics, the subject's input signal is processed normally; this is represented in FIG. 20 as the "boolean and" operator 2040 (i.e., all tests must pass).

An example table of the tests and thresholds for an implementation is provided in Table 1.

TABLE 1

| Signal Quality Test | Threshold |
| --- | --- |
| Powerline Interference (test #1) | 486.6 |
| High Frequency Noise (test #2) | 0.05273 |
| Clean segment not available due to abrupt movement and high frequency bursts (test #3) | 16 second of signal must be available. |

TABLE 1-continued

| Signal Quality Test | Threshold |
| --- | --- |
| Application of tests #1, #2, #3 | Must pass all three |
| Cycle Variability (test #4) | 0.0106 |
| Application of test #1, #2, #3, #4 | Must pass all three |

In North America, with respect to detection of powerline frequency for example, 60 Hz typically is used, while other regions, such as China, EU, India, etc., a powerline frequency of 50 Hz rather than 60 Hz typically is used, so a modification of the score to target that specific frequency may be desired.

Figure 21A:
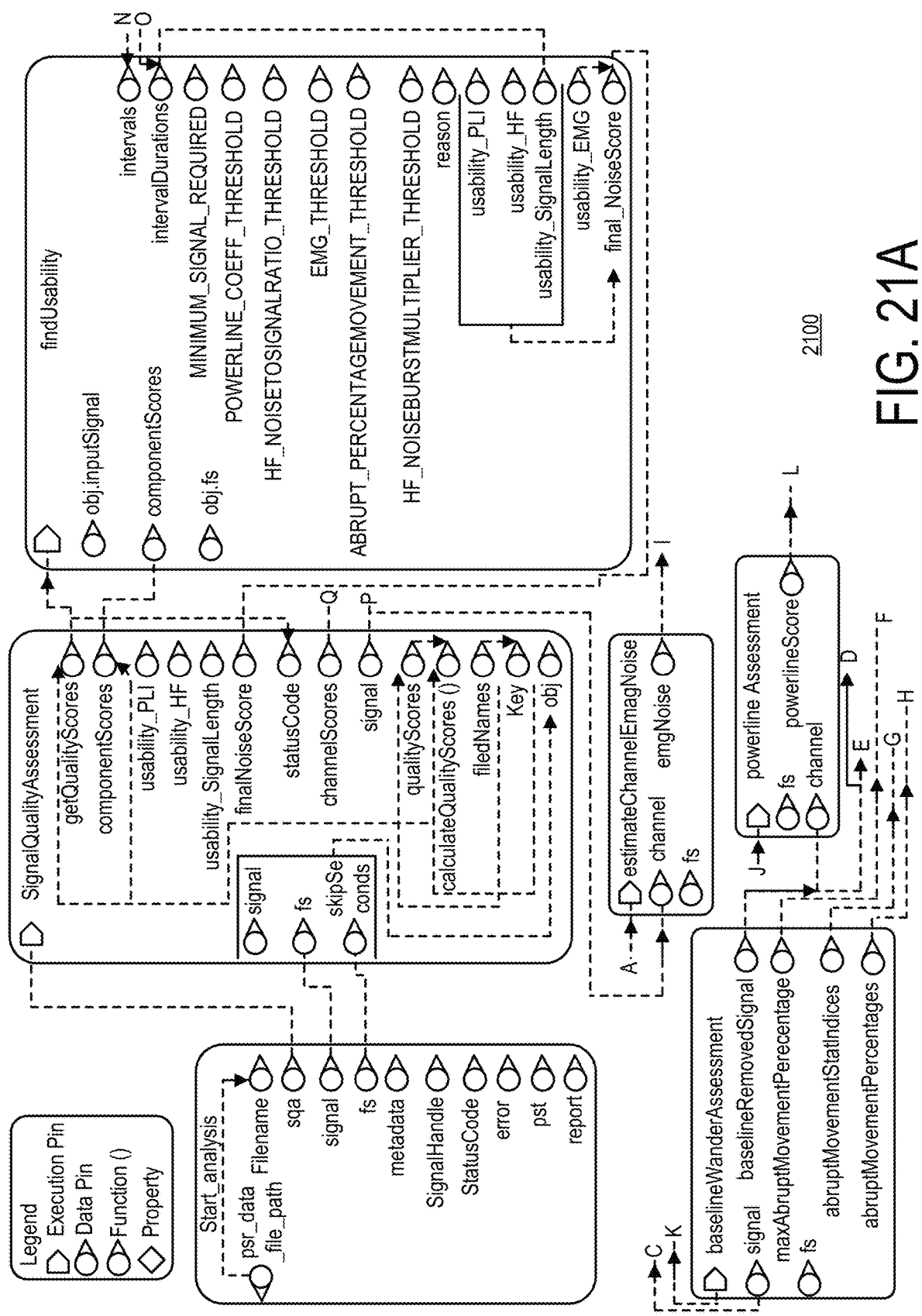
FIGS. 21A and 21B show an architecture and data flow of the of an example signal quality assessment component, in accordance with an illustrative embodiment.
Figure 21B:
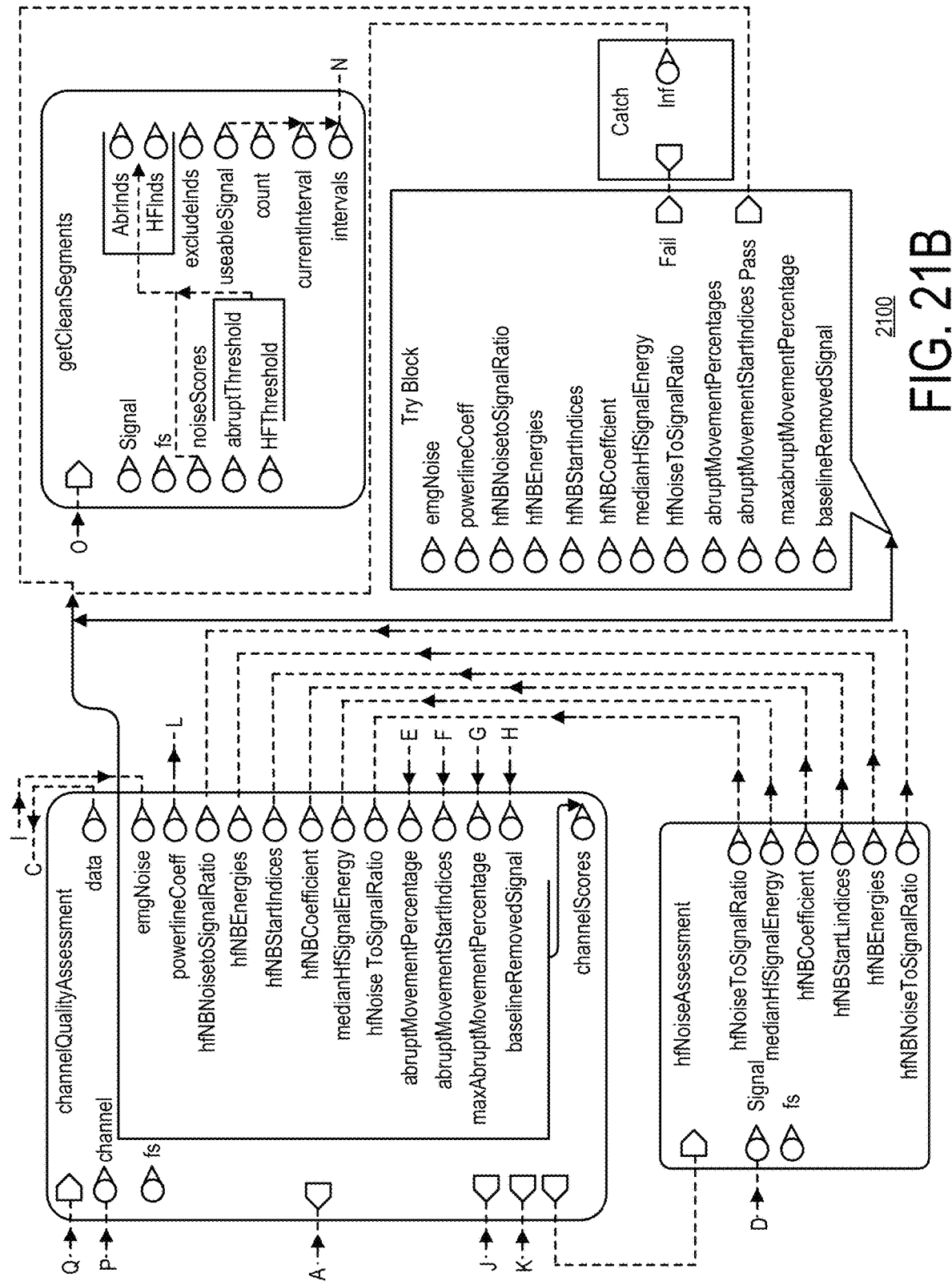

FIGS. 21A and 21B show an architecture and data flow diagram 2100 of an example signal quality assessment component, in accordance with an illustrative embodiment.

Note that the failure of any test does not in an exemplary illustration prevent subsequent execution of assessment system 200; rather, the failure may be reported through the following mechanism, and the PST evaluation is attempted.

The input may comprise the unmodified ORTH1, ORTH2, ORTH3 data as parsed out of the phase space recorder file.

The output may be passed to the DataTransfer APIs (DTAPI) and the report database (RD). In an implementation, the legacy fields "noiseVolume" and "noiseLevelMean" are reused to maintain backwards compatibility within the DTAPI and RD components. In some embodiments, the report databases is configured to store noiseVolume parameter as the cycle variability score if all other signal quality assessment tests pass. If any test (other than cycle variability) fails, then a flag of 10000 is used to represent that state. Cycle variability may have a threshold of 0.0106 in an implementation.

For example, in some embodiments, the noiseLevelMean stores a status code, with the following possible states as provided in Table 2.

TABLE 2

| | |
| --- | --- |
| State = "0" | Indicate a success state in which all signal quality assessment tests (except for cycle variability, which may fail) have passed. |
| State = "1" | Indicate a first failure state in which a 10000 value is present in noiseVolume and the test that failed is due to powerline interference. Powerline interference has a threshold of 486.6 in an implementation. |
| State = "2" | Indicate a second failure state in which a 10000 value is present in noiseVolume and the test that failed is due to high frequency noise. High frequency noise has a threshold of 0.05273 in an implementation. |
| State = "3" | Indicate a third failure state in which a 10000 value is present in noiseVolume and the test that failed is clean signal length; specifically, there must be at least 16 seconds of useable signal, where signal can be deemed unusable by one (or both) of the following two mechanisms:<br>a. high frequency noise bursts, which has a threshold of four times the median energy in an implementation.<br>b. abrupt movement in baseline, which has a threshold of 25% in an implementation. |
| State = "12" | Indicate a fourth failure state in which both the first and second failure states are present. |
| State = "13" | Indicate a fifth failure state in which both the first and third failure states are present. |
| State = "23" | Indicate a sixth failure state in which both the second and third failure states are present. |
| State = "123" | Indicate a seventh failure state in which all first, second and third failure states are present. |

FIG. 22 shows an exemplary computing environment in which example embodiments and aspects, e.g., the assessment system 110, signal quality assessor 305, may be implemented, in accordance with an illustrative embodiment. The computing device environment is only one example of a suitable computing environment and is not intended to suggest any limitation as to the scope of use or functionality.

Numerous other general-purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 22, an exemplary system for implementing aspects described herein includes a computing device, such as computing device 2200. In its most basic configuration, computing device 2200 typically includes at least one processing unit 2202 and memory 2204. Depending on the exact configuration and type of computing device, memory 2204 may be volatile (such as random access memory (RAM)), non-volatile (such as read-only memory (ROM), flash memory, etc.), or some combination of the two. This most basic configuration is illustrated in FIG. 22 by dashed line 2206.

Computing device 2200 may have additional features/functionality. For example, computing device 2200 may include additional storage (removable and/or non-removable) including, but not limited to, magnetic or optical disks or tape. Such additional storage is illustrated in FIG. 22 by removable storage 2208 and non-removable storage 2210.

Computing device 2200 typically includes a variety of computer readable media. Computer readable media can be any available media that can be accessed by the device 2200 and includes both volatile and non-volatile media, removable and non-removable media.

Computer storage media include volatile and non-volatile, and removable and non-removable media implemented in any method or technology for storage of information such as computer readable instructions, data structures, program modules or other data Memory 2204, removable storage 2208, and non-removable storage 2210 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by computing device 2200. Any such computer storage media may be part of computing device 2200.

Computing device 2200 may contain communication connection(s) 2212 that allow the device to communicate with other devices. Computing device 2200 may also have input device(s) 2214 such as a keyboard, mouse, pen, voice input device, touch input device, etc., singularly or in combination. Output device(s) 2216 such as a display, speakers, printer, vibratory mechanisms, etc. may also be included singularly or in combination. All these devices are well known in the art and need not be discussed at length here.

It should be understood that the various techniques described herein may be implemented in connection with hardware components or software components or, where appropriate, with a combination of both. Illustrative types of hardware components that can be used include Graphical Processing Units (GPUs), Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, handheld devices, and wearable devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Further examples of various processing that may be used with the exemplified method and system are described in: U.S. Pat. No. 9,289,150, entitled "Non-invasive Method and System for Characterizing Cardiovascular Systems"; U.S. Pat. No. 9,655,536, entitled "Non-invasive Method and System for Characterizing Cardiovascular Systems"; U.S. Pat. No. 9,968,275, entitled "Non-invasive Method and System for Characterizing Cardiovascular Systems"; U.S. Pat. No. 8,923,958, entitled "System and Method for Evaluating an Electrophysiological Signal"; U.S. Pat. No. 9,408,543, entitled "Non-invasive Method and System for Characterizing Cardiovascular Systems and All-Cause Mortality and Sudden Cardiac Death Risk"; U.S. Pat. No. 9,955,883, entitled "Non-invasive Method and System for Characterizing Cardiovascular Systems and All-Cause Mortality and Sudden Cardiac Death Risk"; U.S. Pat. No. 9,737,229, entitled "Noninvasive Electrocardiographic Method for Estimating Mammalian Cardiac Chamber Size and Mechanical Function"; U.S. Pat. No. 10,039,468, entitled "Noninvasive Electrocardiographic Method for Estimating Mammalian Cardiac Chamber Size and Mechanical Function"; U.S. Pat. No. 9,597,021, entitled "Noninvasive Method for Estimating Glucose, Glycosylated Hemoglobin and Other Blood Constituents"; U.S. Pat. No. 9,968,265, entitled "Method and System for Characterizing Cardiovascular Systems From Single Channel Data"; U.S. Pat. No. 9,910,964, entitled "Methods and Systems Using Mathematical Analysis and Machine Learning to Diagnose Disease"; U.S. Publication No. 2017/0119272, entitled "Method and Apparatus for Wide-Band Phase Gradient Signal Acquisition"; PCT Publication No. WO2017/033164, entitled "Method and Apparatus for Wide-Band Phase Gradient Signal Acquisition"; U.S. Publication No. 2018/0000371, entitled "Non-invasive Method and System for Measuring Myocardial Ischemia, Stenosis Identification, Localization and Fractional Flow Reserve Estimation"; PCT Publication No. WO2017/221221, entitled "Non-invasive Method and System for Measuring Myocardial Ischemia, Stenosis Identification, Localization and Fractional Flow Reserve Estimation"; U.S. Pat. No. 10,292,596, entitled "Method and System for Visualization of Heart Tissue at Risk"; U.S. Publication No. 2018/0249960, entitled "Method and System for Wide-band Phase Gradient Signal Acquisition"; U.S. Publication No. 2019/0214137, filed on Dec. 26, 2018, entitled "Method and System to Assess Disease Using Phase Space Volumetric Objects"; PCT Application No. IB/2018/060708, entitled "Method and System to Assess Disease Using Phase Space Volumetric Objects"; U.S. Patent Publication No. US2019/0117164, entitled "Methods and Systems of De-Noising Magnetic-Field Based Sensor Data of Electrophysiological Signals"; U.S. Publication No. 2019/0214137, filed on Dec. 26, 2018, entitled "Method and System to Assess Disease Using Phase Space Tomography and Machine Learning"; PCT Application No. PCT/IB2018/060709, entitled "Method and System to Assess Disease Using Phase Space Tomography and Machine Learning", U.S. Publication No. 2019/0384757, entitled "Methods and Systems to Quantify and Remove Asynchronous Noise in Biophysical Signals," filed Jun. 18, 2019; U.S. Publication No. 2019/0365265, entitled "Method and System to Assess Pulmonary Hypertension Using Phase Space Tomography and Machine Learning"; U.S. patent application Ser. No. 16/725,402, concurrently filed herewith, entitled "Method and System to Assess Disease Using Phase Space Tomography and Machine Learning" (claiming priority to U.S. Patent Provisional Application Nos. 62/784,984 and 62/835,869); U.S. Patent Application No. 62/784,925, entitled "Method and System to Configure and Use Neural Network To Assess Medical Disease" (claiming priority to U.S. Patent Provisional Application No. 62/784,925); U.S. application Ser. No. 15/653,433, entitled "Discovering Novel Features to Use in Machine Learning Techniques, such as Machine Learning Techniques for Diagnosing Medical Conditions"; U.S. application Ser. No. 15/653,431, entitled "Discovering Genomes to Use in Machine Learning Techniques"; U.S. patent application Ser. No. 16/831,380 (claiming priority to application), entitled "Method and System to Assess Disease Using Dynamical Analysis of Cardiac and Photoplethysmographic Signals"); U.S. patent application Ser. No. 16/831,264 (claiming priority to application), entitled "Method and System to Assess Disease Using Dynamical Analysis of Biophysical Signals", each of which is incorporated by reference herein in its entirety.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with certain embodiments and specific examples, it is not intended that the scope be limited to the particular embodiments set forth, as the embodiments herein are intended in all respects to be illustrative rather than restrictive.

The methods, systems and processes described herein may be used generate stenosis and FFR outputs for use in connection with procedures such as the placement of vascular stents within a vessel such as an artery of a living (e.g., human) subject, and other interventional and surgical system or processes. In one embodiment, the methods, systems and processes described herein can be configured to use the FFR/stenosis outputs to determine and/or modify, intra operation, a number of stents to be placed in a living (e.g., human), including their optimal location of deployment within a given vessel, among others.

Examples of other biophysical signals that may be analyzed in whole, or in part, using the exemplary methods and systems include, but are not limited to, an electrocardiogram (ECG) data set, an electroencephalogram (EEG) data set, a gamma synchrony signal data set; a respiratory function signal data set; a pulse oximetry signal data set; a perfusion data signal data set; a quasi-periodic biological signal data set; a fetal ECG data set; a blood pressure signal; a cardiac magnetic field data set, and a heart rate signal data set.

The exemplary analysis can be used in the diagnosis and treatment of cardiac-related pathologies and conditions and/or neurological-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. One example in the cardiac context is the diagnosis of CAD and its treatment by any number of therapies, alone or in combination, such as the placement of a stent in a coronary artery, performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other disease such as blood or other disorders), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

What is claimed is:

1. A method to acquire a biophysical-signal data set for clinical analysis, the method comprising:
obtaining, by a processor, a biophysical-signal data set of a subject for a measurement, wherein the biophysical-signal data set is acquired via a plurality of surface probes of a non-invasive measurement system over a plurality of corresponding channels and acquired for an acquisition duration suitable for a subsequent assessment;
determining, by one or more cloud-based services or systems, cycle variability noise associated with heart cycle variability using the biophysical-signal data set by, for each channel of the plurality of corresponding channels, calculating a cycle variability noise for the channel, and determining the highest calculated cycle variability noise for any channel as the cycle variability noise for the biophysical data set;
determining, by the one or more cloud-based services or systems, that the entire biophysical-signal data set failed a quality assessment based on the cycle variability noise exceeding a cycle variability noise threshold; and
in response to determining that the entire biophysical signal data set failed the quality assessment:
rejecting, by the one or more cloud-based services or systems, any analyses of the biophysical-signal data set by the one or more cloud-based services or systems; and
reacquiring, by the processor, the biophysical-signal data set.

2. The method of claim 1, further comprising:
acquiring, by one or more acquisition circuits of the measurement system, voltage gradient signals over the plurality of corresponding channels, wherein the voltage gradient signals are acquired at a frequency greater than about 1 kHz; and
generating, by the one or more acquisition circuits, the obtained biophysical-signal data set, or a portion thereof, from the acquired voltage gradient signals.

3. The method of claim 1, wherein the obtained biophysical-signal data set, or an assessed portion thereof, is rejected when a powerline interference parameter for any of the plurality of channels fails a powerline interference condition.

4. The method of claim 3, wherein a powerline coefficient associated with the powerline interference parameter is determined by:
performing, by the processor, a Fourier transform of the obtained biophysical-signal data set, or the portion thereof; and
determining, by the processor, maximum powerline energy at a plurality of frequency ranges.

5. The method of claim 1, further comprising determining, by the one or more cloud-based services or systems, that the biophysical-signal data set failed the quality assessment when one or more asynchronous noise parameters fails an asynchronous noise condition.

6. The method of claim 1, wherein the one or more analyses is a gating stage for an analysis of the subject for coronary artery disease or pulmonary hypertension.

7. The method of claim 1, wherein the biophysical-signal data set comprises a cardiac signal data set.

8. The method of claim 1, wherein the biophysical-signal data set is generated in near real-time as biophysical signals are acquired from sensors in a smart device or in a handheld medical diagnostic equipment.

9. The method of claim 1, wherein the biophysical-signal data set comprises wide-band phase gradient cardiac signal data simultaneously captured from a plurality of surface electrodes placed on surfaces of a body in proximity to a heart of the subject.

10. The method of claim 1, further comprising:
generating, by the processor, a notification of the failed quality assessment.

11. The method of claim 1, further comprising acquiring the biophysical-signal data set via the one or more surface probes, wherein the biophysical-signal data set comprises at least one cardiac signal, at least one neurological signal, and at least one photoplethysmographic signal.

12. The method of claim 1, further comprising:
analyzing the obtained biophysical-signal data set for the presence of pulmonary hypertension.

13. A method to acquire a biophysical-signal data set for clinical analysis, the method comprising:
obtaining, by a processor, a biophysical-signal data set of a subject for a measurement, wherein the biophysical-signal data set is acquired via a plurality of surface probes of a non-invasive measurement system over a plurality of corresponding channels and acquired for an acquisition duration suitable for a subsequent assessment;
determining, by one or more cloud-based services or systems, cycle variability noise associated with heart cycle variability using the biophysical-signal data set by, for each channel of the plurality of corresponding channels, calculating a cycle variability noise for the channel, and determining the highest calculated cycle variability noise for any channel as the cycle variability noise for the biophysical data set;
determining, by the one or more cloud-based services or systems, that the entire biophysical-signal data set did not fail a quality assessment based on the cycle variability noise not exceeding a cycle variability noise threshold; and
in response to determining that the entire biophysical signal data set did not fail the quality assessment, providing, by the processor, the entire biophysical-signal data set for the one or more analyses by the one or more cloud-based services or systems.

14. A system comprising:
one or more processors; and
a memory having instructions stored thereon, wherein execution of the instructions by the one or more processors cause the one or more processors to:
obtain a biophysical-signal data set of a subject for a measurement, wherein the biophysical-signal data set is acquired via a plurality of surface probes of a non-invasive measurement system over a plurality of corresponding channels and acquired for an acquisition duration suitable for a subsequent assessment;
determine cycle variability noise associated with heart cycle variability using the biophysical-signal data set by, for each channel of the plurality of corresponding channels, calculating a cycle variability noise for the channel, and determining the highest calculated cycle variability noise for any channel as the cycle variability noise for the biophysical data set;

determine that the entire biophysical-signal data set failed a quality assessment based on the cycle variability noise exceeding a cycle variability noise threshold; and in response to determining that the entire biophysical signal data set failed the quality assessment:
  reject any analyses of one or more cloud-based services or systems; and
  reacquire the biophysical-signal data set.

15. A non-transitory computer readable medium having instructions stored thereon, wherein execution of the instruction by one or more processors, cause the one or more processors to:

obtain a biophysical-signal data set of a subject for a measurement wherein the biophysical-signal data set is acquired via a plurality of surface probes of a non-invasive measurement system over a plurality of corresponding channels and acquired for an acquisition duration suitable for a subsequent assessment;

determine cycle variability noise associated with heart cycle variability using the biophysical-signal data set by, for each channel of the plurality of corresponding channels, calculating a cycle variability noise for the channel, and determining the highest calculated cycle variability noise for any channel as the cycle variability noise for the biophysical data set;

determine that the entire biophysical-signal data set failed a quality assessment based on the cycle variability noise exceeding a cycle variability noise threshold; and in response to determining that the entire biophysical signal data set failed the quality assessment:
  reject any analyses of one or more cloud-based services or systems; and
  reacquire the biophysical-signal data set.

16. A system comprising:
one or more processors; and
a memory having instructions stored thereon, wherein execution of the instructions by the one or more processors cause the one or more processors to:

obtain a biophysical-signal data set of a subject for a measurement, wherein the biophysical-signal data set is acquired via a plurality of surface probes of a non-invasive measurement system over a plurality of corresponding channels and acquired for an acquisition duration suitable for a subsequent assessment;

determine cycle variability noise associated with heart cycle variability using the biophysical-signal data set by, for each channel of the plurality of corresponding channels, calculating a cycle variability noise for the channel, and determining the highest calculated cycle variability noise for any channel as the cycle variability noise for the biophysical data set;

determine that the entire biophysical-signal data set did not fail a quality assessment based on the cycle variability noise not exceeding a cycle variability noise threshold; and in response to determining that the entire biophysical signal data set did not fail the quality assessment, provide the biophysical-signal data set for one or more analyses by one or more cloud-based services or systems.

17. A non-transitory computer readable medium having instructions stored thereon, wherein execution of the instruction by one or more processors, cause the one or more processors to:

obtain a biophysical-signal data set of a subject for a measurement, wherein the biophysical-signal data set is acquired via a plurality of surface probes of a non-invasive measurement system over a plurality of corresponding channels and acquired for an acquisition duration suitable for a subsequent assessment;

determine cycle variability noise associated with heart cycle variability using the biophysical-signal data set by, for each channel of the plurality of corresponding channels, calculating a cycle variability noise for the channel, and determining the highest calculated cycle variability noise for any channel as the cycle variability noise for the biophysical data set;

determine that the entire biophysical-signal data set did not fail a quality assessment based on the cycle variability noise not exceeding a cycle variability noise threshold; and in response to determining that the biophysical signal data set did not fail the quality assessment, provide the entire biophysical-signal data set for one or more analyses by one or more cloud-based services or systems.

* * * * *